(12) United States Patent
Fyfe

(10) Patent No.: US 10,882,859 B2
(45) Date of Patent: *Jan. 5, 2021

(54) KINASE INHIBITORS

(71) Applicant: Topivert Pharma Limited, London (GB)

(72) Inventor: Matthew Colin Thor Fyfe, London (GB)

(73) Assignee: TOPIVERT PHARMA LIMITED, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/710,074

(22) Filed: Dec. 11, 2019

(65) Prior Publication Data

US 2020/0223843 A1 Jul. 16, 2020

Related U.S. Application Data

(63) Continuation of application No. 15/772,887, filed as application No. PCT/GB2016/053392 on Nov. 2, 2016, now Pat. No. 10,556,901.

(30) Foreign Application Priority Data

Nov. 3, 2015 (GB) .................................. 1519382.4
Apr. 21, 2016 (GB) .................................. 1606971.8

(51) Int. Cl.
| | |
|---|---|
| *C07D 471/04* | (2006.01) |
| *A61K 45/06* | (2006.01) |
| *A61P 27/02* | (2006.01) |
| *A61P 11/06* | (2006.01) |
| *A61P 29/00* | (2006.01) |

(52) U.S. Cl.
CPC ............ *C07D 471/04* (2013.01); *A61K 45/06* (2013.01); *A61P 11/06* (2018.01); *A61P 27/02* (2018.01); *A61P 29/00* (2018.01)

(58) Field of Classification Search
CPC ...... C07D 471/303; A61K 45/06; A61P 27/02
USPC .......................................................... 514/303
See application file for complete search history.

(56) References Cited

U.S. PATENT DOCUMENTS

| | | | |
|---|---|---|---|
| 10,022,376 | B2 | 7/2018 | Coe et al. |
| 10,196,393 | B2 * | 2/2019 | Fatheree .............. C07D 471/04 |
| 2010/0267751 | A1 | 10/2010 | Beals et al. |
| 2013/0029968 | A1 | 1/2013 | Coe et al. |
| 2014/0246343 | A1 | 9/2014 | Sebille et al. |
| 2017/0071946 | A1 | 3/2017 | Coe et al. |
| 2017/0121327 | A1 | 5/2017 | Fatheree et al. |
| 2017/0145044 | A1 | 5/2017 | Hudson et al. |
| 2018/0319791 | A1 | 11/2018 | Fyfe |
| 2018/0370963 | A1 | 12/2018 | Fyfe |

FOREIGN PATENT DOCUMENTS

| | | |
|---|---|---|
| WO | 2013/014567 A1 | 1/2013 |
| WO | WO-2013014567 A1 * | 1/2013 ........... C07D 471/04 |
| WO | 2015/173683 A1 | 11/2015 |
| WO | 2016/191524 A1 | 12/2016 |
| WO | 2017/077283 A1 | 5/2017 |
| WO | 2017/189822 A1 | 11/2017 |

OTHER PUBLICATIONS

ASCRS, Crohn's Disease Expanded Version. American Society of Colon and Rectal Surgeons. Retrieved online at: https://www.fascrs.org/patients/disease-condition/crohns-disease-expanded-version. 12 pages, Feb. 16, 2015.

Barnes, New anti-inflammatory targets for chronic obstructive pulmonary disease. Nat Rev Drug Discov. Jul. 2013;12(7):543-59.

Beattie et al., Intestinally-restricted Janus Kinase inhibition: a potential approach to maximize the therapeutic index in inflammatory bowel disease therapy. J Inflamm (Lond). Dec. 6, 2017;14:28. 11 pages.

Boland et al., Update on Janus kinase antagonists in inflammatory bowel disease. Gastroenterol Clin North Am. Sep. 2014;43(3):603-17.

Casanova et al., Inborn errors of human JAKs and STATs. Immunity. Apr. 20, 2012;36(4):515-28.

Clark et al., Discovery and development of Janus kinase (JAK) inhibitors for inflammatory diseases. J Med Chem. 2013, 16 pages, prepublication version. doi: 10.1021/jm401490p.

Dupont et al., Filgotinib, JAK1-Selective Inhibitor, Represses Similarly JAK1/STAT3 Pathway in the Colon of Mice with DSS-Induced Colitis and in Cultures of Colon Biopsies from Inflammatory Bowel Disease Patients. Inflamm Res. 2015;64(Suppl 2):S202, Abstract B252.

(Continued)

*Primary Examiner* — Rita J Desai
(74) *Attorney, Agent, or Firm* — Seed IP Law Group LLP

(57) ABSTRACT

There are provided compounds of formula I,

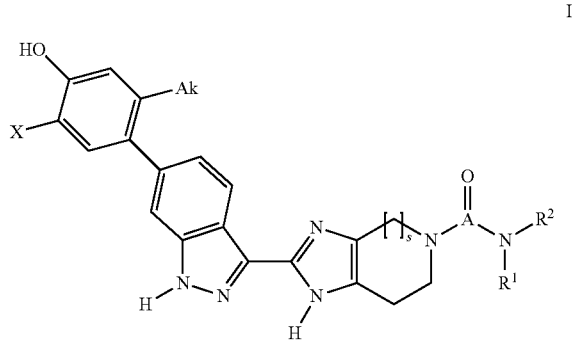

wherein X, Ak, s, A, $R^1$ and $R^2$ have meanings given in the description, which compounds have antiinflammatory activity (e.g. through inhibition of one or more of members of the JAK family) and have use in therapy, including in pharmaceutical combinations, especially in the treatment of inflammatory diseases, including inflammatory diseases of the lung, eye and intestines.

21 Claims, No Drawings

(56) References Cited

OTHER PUBLICATIONS

Farraye et al., AGA medical position statement on the diagnosis and management of colorectal neoplasia in inflammatory bowel disease. Gastroenterology. Feb. 2010;138(2):738-45.

Fenwick et al., Effect of JAK Inhibitors on Release of CXCL9, CXCL10 and CXCL11 from Human Airway Epithelial Cells. PLoS One. Jun. 19, 2015;10(6):e0128757. 18 pages.

Flanagan et al., Discovery of CP-690,550: a potent and selective Janus kinase (JAK) inhibitor for the treatment of autoimmune diseases and organ transplant rejection. J Med Chem. Dec. 23, 2010;53(24):8468-84.

Foloppe et al., Identification of a buried pocket for potent and selective inhibition of Chk1: prediction and verification. Bioorg Med Chem. Mar. 15, 2006;14(6):1792-804.

Fukuyama et al., Inhibitors Tofacitinib and Oclacitinib Display Impressive Antipruritic and Anti-Inflammatory Responses in a Model of Allergic Dermatitis. J Pharmacol Exp Ther. Sep. 2015;354(3):394-405.

Galien et al., Exploration of GLPG0634, the First Selective JAK1 Inhibitor, in Inflammatory Bowel Disease Is Supported by Early Clinical Results and Mouse DSS-Colitis Data. AGA Abstracts, p. S-49, Abstract No. 188. (2014).

Huang et al., Evaluation of JAK inhibition with topical tofacitinib in an experimental autoimmune uveitis model (EAU). ARVO Annual Meeting Abstract. Investigative Ophthalmology & Visual Science. Jun. 2013;54, Abstract 2536. 1 page.

Huang et al., Immunomodulatory effect of the topical ophthalmic Janus kinase inhibitor tofacitinib (CP-690,550) in patients with dry eye disease. Ophthalmology. Jul. 2012;119(7):e43-50.

IrishHealth, Age-related macular degeneration (ARMD). Irishhealthpro.com, retrieved online at: http://www.irishhealthpro.com/article.html?con=198. 6 pages, Apr. 3, 2004.

Jones et al., Design and Synthesis of a Pan-Janus Kinase Inhibitor Clinical Candidate (PF-06263276) Suitable for Inhaled and Topical Delivery for the Treatment of Inflammatory Diseases of the Lungs and Skin. J Med Chem. 2016, 20 pages, prepublication version, doi: 10.1021/acs.jmedchem.6b01634.

Jones, Novel JAK Inhibitors for Inhaled and Topical Delivery. FMC2015, Frontiers in Medicinal Chemistry, p. 73, Abstract No. IL23, (2015).

Khor et al., Genetics and pathogenesis of inflammatory bowel disease. Nature. Jun. 15, 2011;474(7351):307-17.

Lees et al., New IBD genetics: common pathways with other diseases. Gut. Dec. 2011;60(12):1739-53.

Liew et al., Tofacitinib (CP-690,550), a Janus kinase inhibitor for dry eye disease: results from a phase 1/2 trial. Ophthalmology. Jul. 2012;119(7):1328-35.

Merciris et al., GLPG0634, the First Selective JAK1 Inhibitor, Shows Strong Activity in the Mouse DSS-Induced Colitis Model. Galapagos. Poster No. P072, 1 page. Retrieved online at: www.glpg.com, (2014).

Mesa et al., Ruxolitinib. Nat Rev Drug Discov. Feb. 1, 2012;11(2):103-4.

Nord, Cystic Fibrosis. National Organization for Rare Disorders. Retrieved online at: https://rarediseases.org/rare-diseases/cystic-fibrosis/ 19 pages, Nov. 9, 2010.

Nord, Ulcerative Colitis. National Organization for Rare Disorders. Retrieved online at: https://rarediseases.org/rare-diseases/ulcerative-colitis/ 19 pages, Jun. 20, 2001.

Norman, Selective JAK inhibitors in development for rheumatoid arthritis. Expert Opin Investig Drugs. 2014, 11 pages, prepublication version, doi: 10.1517/13543784.2014.918604.

Ongenaert et al., The JAK1-Selective Inhibitor, Filgotinib, Reverses the Disease Signature of Colon Mucosa in Experimental Colitis. Digestive Disease Week (DDW) 2016, Abstract Sa1844.

Panés et al., Randomized trial of tofacitinib in active ulcerative colitis: analysis of efficacy based on patient-reported outcomes. BMC Gastroenterol. Feb. 5, 2015;15:14.

Sandborn et al., Tofacitinib, an oral Janus kinase inhibitor, in active ulcerative colitis. N Engl J Med. Aug. 16, 2012;367(7):616-24.

Stevenson et al., Effects of topical Janus kinase inhibition on ocular surface inflammation and immunity. Cornea. Feb. 2014;33(2):177-83.

Stuart et al., Therapeutic inhibition of JAK activity inhibits progression of gastrointestinal tumors in mice. Mol Cancer Ther. Feb. 2014;13(2):468-74.

Thoma et al., Selective inhibitors of the Janus kinase Jak3—Are they effective? Bioorg Med Chem Lett. Oct. 1, 2014;24(19):4617-4621.

Uckun et al., Anti-inflammatory activity profile of JANEX-1 in preclinical animal models. Bioorg Med Chem. Feb. 1, 2008;16(3):1287-98.

Vuitton et al., Janus kinase inhibition with tofacitinib: changing the face of inflammatory bowel disease treatment. Curr Drug Targets. Nov. 2013;14(12):1385-91.

Wang et al., A novel chemotype of kinase inhibitors: Discovery of 3,4-ring fused 7-azaindoles and deazapurines as potent JAK2 inhibitors. Bioorg Med Chem Lett. Jan. 1, 2010;20(1):153-6.

Yamaoka et al., Targeting the Janus kinases in rheumatoid arthritis: focus on tofacitinib. Expert Opin Pharmacother. Jan. 2014;15(1):103-13.

Zhang et al., JAK2 rs10758669 polymorphisms and susceptibility to ulcerative colitis and Crohn's disease: a meta-analysis. Inflammation. Jun. 2014;37(3):793-800.

Zuccotto et al., Through the "Gatekeeper Door": Exploiting the Active Kinase Conformation. J Med Chem. Apr. 8, 2010;53(7):2681-94.

International Search Report and Written Opinion for Application No. PCT/GB2016/053387, dated Dec. 14, 2016. 9 pages.

International Search Report and Written Opinion for Application No. PCT/GB2016/053392, dated Jan. 5, 2017. 8 pages.

U.S. Appl. No. 15/772,861, filed May 2, 2018, 2018-0319791, Published.

U.S. Appl. No. 15/772,887, filed May 2, 2018, 2018-0370963, Allowed.

* cited by examiner

KINASE INHIBITORS

This application is a continuation of U.S. patent application Ser. No. 15/772,887, which is U.S. national stage filing, under 35 U.S.C. § 371(c), of International Application No. PCT/GB2016/053392, filed on Nov. 2, 2016, which, in turn, claims priority to United Kingdom Patent Application No. 1606971.8, filed on Apr. 21, 2016; and United Kingdom Patent Application No. 1519382.4, filed on Nov. 3, 2015. The entire contents of each of the aforementioned applications are incorporated herein by reference.

This invention relates, inter alia, to compounds which are antiinflammatory agents (e.g., through inhibition of one or more of members of the Janus kinase (JAK) family). The invention also relates to the use of such compounds in therapy, including in mono- and combination therapies, especially in the treatment of inflammatory diseases, including inflammatory diseases of the lung (such as asthma and chronic obstructive pulmonary disease (COPD)), eye (such as uveitis or dry eye disease (DED, also known as keratoconjunctivitis sicca and xerophthalmia)) and gastrointestinal tract (such as Crohn's disease (CD) and ulcerative colitis (UC)).

The listing or discussion of an apparently prior-published document in this specification should not necessarily be taken as an acknowledgement that the document is part of the state of the art or is common general knowledge.

The JAKs are a family of intracellular tyrosine kinases that play an essential role in the signalling of numerous cytokines implicated in the pathogenesis of inflammatory diseases and are critical to both innate and adaptive immunities (Clark, J. D.; Flanagan, M. E.; Telliez, J.-B. *J. Med. Chem.* 2014, 57, 5023-5038). The family comprises four members, JAK1, JAK2 and TYK2—all of which are expressed ubiquitously—and JAK3, found only in hematopoietic cells. These enzymes show high sequence homology and are constitutively bound to the cytoplasmic tail of cytokine receptors. When a cytokine binds to its receptor, multimerization (dimerization or higher order complexes) of receptor subunits occurs, bringing the JAK enzymes associated with each subunit proximal to one another. JAK family members then auto- and/or trans-phosphorylate, which triggers a series of phosphorylation events resulting ultimately in the phosphorylation and activation of signal transducers and activators of transcription (STAT) proteins. A phosphorylated STAT dimer then translocates to the nucleus of the cell where it binds to target genes to modulate their expression and alter cellular function. Importantly, there are no known compensatory pathways around JAK/STAT signalling and, as such, the JAK enzymes are essential in regulating the cytokines that signal through these pathways. As a result of their critical role in cytokine signalling, the JAK enzymes have become targets for drug discovery and development endeavours that have given rise to two marketed products, tofacitinib and ruxolitinib, as well as various compounds in development (Norman, P. *Expert Opin. Investig. Drugs* 2014, 23, 1067-1077). Of the two commercialised products, pan-JAK inhibitor tofacitinib (Flanagan, M. E., et al. *J. Med. Chem.* 2010, 53, 8468-8484) is more relevant for inflammatory diseases, being marketed for the treatment of rheumatoid arthritis (Yamaoka, K.; Tanaka, Y. *Expert Opin. Pharmacother.* 2014, 15, 103-113) and investigated in the clinic for inflammatory bowel diseases (IBD), such as UC (Sandborn, W. J., et al. *New Engl. J. Med.* 2012, 367, 616-624; Vuitton, L.; Koch, S.; Peyrin-Biroulet, L. *Curr. Drug Targ.* 2013, 14, 1385-1391; Panes, J., et al. *BMC Gastroenterol.* 2015, 15, 14), while JAK1/JAK2 inhibitor ruxolitinib is marketed for the treatment of myelofibrosis (Mesa, R. A.; Yasothan, U.; Kirkpatrick, P. *Nat. Rev. Drug Discov.* 2012, 11, 103-104). Tofacitinib and other JAK inhibitors have been mooted as potential therapies for other immunological disorders, including COPD (Barnes, P. *J. Nat. Rev. Drug Discov.* 2013, 12, 543-559; Fenwick, P. S., et al. *PLoS ONE* 2015, 10(6), e0128757), DED (Beals, C. R.; Woldemussie, E. US Patent Application Publication US 2010/0267751, 21 Oct. 2010; Liew, S. H., et al. *Ophthalmology* 2012, 119, 1328-1335; Huang, J.-F., et al. *Ophthalmology* 2012, 119, e43-e50) and uveitis (Huang, J.-F.; Zhang, Y.; Hirakawa, B., 2013 *Association for Research in Vision and Ophthalmology Annual Meeting*, Seattle, USA, 5-9 May 2013, Abstract 2536).

JAK kinases function as homo or heterodimers dimers which are specific to cytokine receptor subunits. For example, JAK1-JAK3 heterodimers associate with the γ-common chain of receptors to control signalling associated with IL2, IL4, IL7, IL9, IL15 and IL21, cytokines predominantly associated with adaptive immune functions. JAK1, however, also functions as a heterodimer with JAK2 and TYK2 to regulate signalling through a wide array of cytokine receptors. In this manner, JAK1 modulates the signalling of several proinflammatory cytokines associated with the innate immune response, such as IL6 and the type I interferons. JAK2 is the only member of the JAK family that can operate as a homodimer. In this combination, JAK2 controls the signalling of various cytokines and growth factors, such as IL3, IL5, granulocyte macrophage colony-stimulating factor, erythropoietin and thrombopoietin.

The potential importance of JAK1 to IBD is emphasised by the fact that two selective JAK1 inhibitors, filgotinib (GLPG0634) and ABT-494, are in phase 2 clinical trials for CD (Galien, R., et al. *Gastroenterology* 2014, 146 (*Suppl* 1), S-49, Abstract 188). Filgotinib is of particular interest for the treatment of IBD, given that, when colon biopsies from IBD patients were treated with this compound, the regulation of IL6 and MX1 expression and a relationship with STAT3 phosphorylation were observed (Dupont, S., et al. *Inflamm. Res.* 2015, 64 (*Suppl* 2), S202, Abstract B252). Furthermore, filgotinib has demonstrated efficacy in the mouse dextran sodium sulfate-induced model of colitis, with efficacy being associated with the inhibition of STAT3 phosphorylation in the inflamed colon (Merciris, D., et al. *9th Congress of the European Crohn's and Colitis Organisation*, Copenhagen, Denmark, 20-22 Feb. 2014, Abstract P072). JAK2 is implicated in that polymorphisms of the corresponding gene are risk factors for both CD and UC, especially in Caucasians (Zhang, J. X., et al. *Inflammation* 2014, 37, 793-800). In addition, many components of the IL23 pathway, including JAK2 and TYK2, are true IBD susceptibility genes, suggesting a critical role for this pathway in maintaining intestinal immune homeostasis (Lees, C. W., et al. *Gut* 2011, 60, 1739-1753; Khor, B.; Gardet, A.; Xavier, R. J. *Nature* 2011, 474, 307-317). It should also be noted that, when administered orally, the JAK1/2 inhibitor AZD1480 inhibited colitis-associated colon cancer, a model of inflammation-driven tumorigenesis (Stuart, E., et al. *Mol. Cancer Ther.* 2014, 13, 468-474). This is important, given that patients with UC and CD of the colon have an increased risk of developing colorectal cancer (Farraye, F. A., et al. *Gastroenterology* 2010, 138, 738-745). The importance of JAK3 in immune homeostasis has been underscored by the observations that loss-of-function mutations in humans result in a severe combined immunodeficiency phenotype (Casanova, J.-L.; Holland, S. M.; Notarangelo, L. D. *Immunity* 2012, 36, 515-528). Furthermore, the selective JAK3 inhibitor JANEX1 demonstrated activity in preclinical models of colitis (Uckun, F. M., et al. *Bioorg. Med. Chem.* 2008, 16, 1287-1298). Nonetheless, it has been indicated that JAK3 inhibition alone is not sufficient to achieve maximal anti-inflammatory efficacy and that additional inhibition of JAK1 is necessary to enhance cellular activity (Thoma, G.; Drückes, P.; Zerwes, H.-G. *Bioorg. Med. Chem. Lett.* 2014, 24, 4617-4621).

As indicated above, all of the JAK enzymes are associated with IBD in one way or another. As such, pan-JAK inhibitors may offer the best chance of achieving efficacy in patients. In this regard, the pan-JAK inhibitor tofacitinib has demonstrated (Boland, B. S.; Sandborn, W. J.; Chang, J. T. *Gastroenterol. Clin. N. Am.* 2014, 43, 603-617) dose-dependent efficacy in Phase 2 clinical trials for UC, albeit at higher doses than that approved for the treatment of rheumatoid arthritis (5 mg twice-daily). Phase 3 studies are currently underway to evaluate the efficacy of this compound (10 mg twice-daily) as an induction therapy in patients with active UC, and at 5 and 10 mg twice-daily as a maintenance therapy in UC patients who have responded to tofacitinib induction therapy. However, as a result of systemic JAK inhibition, tofacitinib therapy is associated with dose-limiting side effects, in particular, opportunistic infections, dose-related lipid abnormalities and bone marrow suppression, which is mediated through JAK2 inhibition and results in anaemia, thrombocytopenia and neutropenia. Thus, although tofacitinib has demonstrated efficacy in UC patients, there is a need for efficacious agents exhibiting an improved side effect profile.

When administered by inhalation, clinical pan-JAK inhibitor PF06263276 (Reference Compound; Coe, J. W., et al. WO2013/014567, 31 Jan. 2013) has been reported to attenuate IL6-stimulated pSTAT induction in mouse lung. In addition, following topical administration, this compound reduced mouse ear swelling induced by an IL23 injection (Jones, P. *Frontiers in Medicinal Chemistry* 2015, Antwerp, Belgium, 14-16 Sep. 2015, Abstract IL23). The crystal structure of PF06263276 bound to JAK2 reveals that this compound interacts with the kinase employing the Type 1.5 binding mode (Foloppe, N., et al. *Bioorg. Med. Chem.* 2006, 14, 1792-1804; Zuccotto, F., et al. *J. Med. Chem.* 2010, 53, 2681-2694; Wang, T., et al. *Bioorg. Med. Chem. Lett.* 2010, 20, 153-156) such that its "Northwestern" phenol terminus acts as both a hydrogen bond donor and a hydrogen bond acceptor, binding it deeply within a hydrophobic pocket. The binding mode observed results in PF06263276 exhibiting slow-offset kinetics and an extended cellular duration of action.

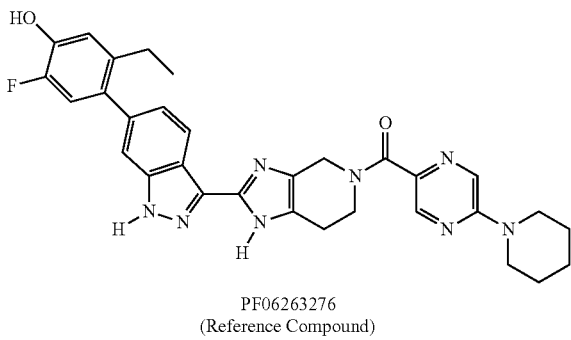 [SMILES: CCc1cc(O)c(F)cc1-c1ccc2c(-c3nc4c([nH]3)CCN(C(=O)c3cnc(N5CCCCC5)cn3)C4)n[nH]c2c1]

PF06263276
(Reference Compound)

We have now discovered, surprisingly, that certain ureas inhibit one or more of the JAK enzymes and therefore possess strong anti-inflammatory properties.

Thus, according to a first aspect of the invention, there is provided a compound of formula I,

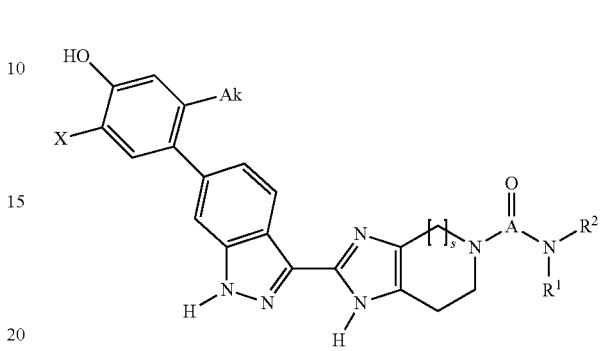

I wherein:

X represents halo;

Ak represents $C_{1-6}$ alkyl optionally substituted by one or more fluorine atoms;

s represents 1 or 2;

A represents C or S(=O);

$R^1$ and $R^2$ each independently represents H, $C_{1-6}$ alkyl, $C_{3-7}$ cycloalkyl, aryl, heteroaryl, or heterocyclyl, which latter five groups are optionally substituted by one or more substituents selected from halo, cyano, $CO_2H$, oxo, $NR^3SO_2R^4$, —N=S(O)($R^4$)$_2$, S(O)$_m R^5$, P(O)($R^4$)$_2$, C(O)$NR^5R^6$, S(O)$_2NR^5R^6$, —(OCH$_2$CH$_2$)$_{0-4}$OR$^5$, —(CH$_2$)$_{0-4}$—$NR^5R^6$, $C_{1-6}$ alkyl, $C_{2-6}$ alkenyl, $C_{2-6}$ alkynyl, $C_{3-7}$ cycloalkyl, aryl, heteroaryl or heterocyclyl, which latter seven groups are optionally substituted by one or more substituents selected from halo, cyano, $CO_2H$, $C_{1-4}$ alkyl, $C_{1-4}$ alkoxy, oxo and hydroxy;

or $R^1$ and $R^2$, together with the N-atom to which they are attached, form a 4- to 7-membered heterocyclic group that is fully saturated or partially unsaturated and which heterocyclic group contains one N atom (the atom to which $R^1$ and $R^2$ are attached) and, optionally, one or more further heteroatoms selected from O, S and N, and which heterocyclic group is optionally fused to a benzene or heteroaromatic ring, and which heterocyclic group is optionally substituted by one or more substituents selected from halo, hydroxy, oxo, $CO_2H$, $NR^3SO_2R^4$, $S(O)_m R^5$, $C(O)NR^5R^6$, —(CH$_2$)$_{0-4}$—$NR^5R^6$, —(OCH$_2$CH$_2$)$_{0-4}$OR$^5$, $C_{1-4}$ alkyl, $C_{1-4}$ alkoxy, aryl, heteroaryl, and heterocyclyl, which latter five groups are optionally substituted by one or more substituents selected from halo, cyano, $CO_2H$, $C_{1-4}$ alkyl, $C_{1-4}$ alkoxy, oxo and hydroxy;

$R^3$ represents H or $C_{1-4}$ alkyl optionally substituted by one or more substituents selected from halo, hydroxy and $C_{1-2}$ alkoxy;

$R^4$ represents $C_{1-4}$ alkyl, $C_{3-7}$ cycloalkyl, aryl, heteroaryl or heterocyclyl, which latter five groups are optionally substituted by one or more substituents selected from halo, cyano, $CO_2H$, $C_{1-4}$ alkyl, oxo, hydroxy and $C_{1-4}$ alkoxy;

$R^5$ and $R^6$ each independently represent H, $C_{1-6}$ alkyl, $C_{3-7}$ cycloalkyl, aryl, heteroaryl, or heterocyclyl, which latter five groups are optionally substituted by one or more substituents selected from halo, cyano, $CO_2H$, oxo, hydroxy, $C_{1-4}$ alkyl, $C_{1-4}$ alkoxy, $S(O)_p R^7$, $C(O)NR^aR^b$ and —(CH$_2$)$_{0-4}$—$NR^aR^b$, or —[C($R^{6b}$)($R^{6c}$)$CH_2$Z]$_{1-12}$—$CH_2CH_2$—$R^{6a}$ or —C($R^{6b}$)($R^{6c}$)—[$C^{1-5}$ alkylene]-$R^{6a}$;

or $R^5$ and $R^6$, together with the N-atom to which they are attached, form a 4- to 7-membered heterocyclic group that is fully saturated or partially unsaturated and which heterocyclic group contains one N atom (the atom to which $R^5$ and $R^6$ are attached) and, optionally, one or more further heteroatoms selected from O, S and N, and which heterocyclic group is optionally substituted by one or more substituents selected from halo, hydroxy, oxo, $CO_2H$, $S(O)_pR^7$, $C(O)NR^aR^b$, —$(CH_2)_{0-4}$—$NR^aR^b$, —$(OCH_2CH_2)_{0-4}$$OR^c$, $C_{1-4}$ alkyl, $C_{1-4}$ alkoxy, aryl, heteroaryl and heterocyclyl, which latter five groups are optionally substituted by one or more substituents selected from halo, cyano, $CO_2H$, $C_{1-4}$ alkyl, $C_{1-4}$ alkoxy, oxo and hydroxy;

Z represents, independently upon each occurrence, O, C(O)N($R^8$) or N($R^8$)C(O);

$R^{6a}$ represents $OR^{7a}$, —$S(O)_pR^7$, $N(R^{7b})R^{7c}$ or $CO_2H$;

$R^{6b}$, $R^{6c}$ and $R^8$ independently represent H or methyl;

$R^a$, $R^b$ and $R^c$ independently represent H or $C_{1-4}$ alkyl optionally substituted by one or more substituents selected from halo, hydroxy and —$CO_2H$, or $R^a$ and $R^b$, together with the N-atom to which they are attached, form a 4- to 7-membered heterocyclic group that is fully saturated, partially unsaturated or fully aromatic and which heterocyclic group contains one N atom (the atom to which $R^a$ and $R^b$ are attached) and, optionally, one or more further heteroatoms selected from O, S and N, and which heterocyclic group is optionally substituted by one or more substituents selected from halo, hydroxy, oxo, $CO_2H$, $C_{1-4}$ alkyl, $C_{1-4}$ alkoxy and $C_{1-4}$ hydroxyalkyl;

$R^7$ represents $C_{1-4}$ alkyl optionally substituted by one or more substituents selected from halo, hydroxy and $C_{1-4}$ alkoxy;

$R^{7a}$ to $R^{7c}$ independently represent H or $C_{1-4}$ alkyl optionally substituted by one or more halo atoms or by —$CO_2H$, or $R^{7b}$ and/or $R^{7c}$ represents —[$C_a$ alkylene]-[$C_b$ alkylene]-$OR^{7d}$, or $R^{7b}$ and $R^{7c}$ together with the N-atom to which they are attached, form a 4- to 7-membered heterocyclic group that is fully saturated, partially unsaturated or fully aromatic and which heterocyclic group contains one N atom (the atom to which $R^{7b}$ and $R^{7c}$ are attached) and, optionally, one or more further heteroatoms selected from O, S and N, and which heterocyclic group is optionally substituted by one or more substituents selected from halo, hydroxy, oxo, $CO_2H$, $C_{1-4}$ alkyl, $C_{1-4}$ alkoxy and $C_{1-4}$ hydroxyalkyl; a and b independently represent an integer selected from 1, 2 and 3, wherein the sum of a and b is 2, 3 or 4;

$R^{7d}$ represents H or $C_{1-4}$ alkyl optionally substituted by one or more halo atoms;

m and p represent, independently upon each occurrence, 0, 1 or 2;

or a pharmaceutically acceptable salt, solvate or isotopic derivative thereof, which compounds may be referred to hereinafter as "the compounds of the invention".

Pharmaceutically acceptable salts that may be mentioned include acid addition salts and base addition salts. Such salts may be formed by conventional means, for example by reaction of a free acid or a free base form of a compound of formula I with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound of formula I in the form of a salt with another counter-ion, for example using a suitable ion exchange resin.

Examples of pharmaceutically acceptable salts include acid addition salts derived from mineral acids and organic acids, and salts derived from metals.

For the avoidance of doubt, compounds of formula I may contain the stated atoms in any of their natural or non-natural isotopic forms. In this respect, embodiments of the invention that may be mentioned include those in which:

(a) the compound of formula I is not isotopically enriched or labelled with respect to any atoms of the compound; and (b) the compound of formula I is isotopically enriched or labelled with respect to one or more atoms of the compound.

References herein to an "isotopic derivative" relate to the second of these two embodiments. In particular embodiments of the invention, the compound of formula I is isotopically enriched or labelled (with respect to one or more atoms of the compound) with one or more stable isotopes. Thus, the compounds of the invention that may be mentioned include, for example, compounds of formula I that are isotopically enriched or labelled with one or more atoms such as deuterium or the like.

Compounds of formula I may exhibit tautomerism. All tautomeric forms and mixtures thereof are included within the scope of the invention.

Unless otherwise specified, alkyl groups and alkoxy groups as defined herein may be straight-chain or, when there is a sufficient number (i.e. a minimum of three) of carbon atoms, be branched. Particular alkyl groups that may be mentioned include, for example, methyl, ethyl, n-propyl, iso-propyl, butyl, n-butyl and tert-butyl. Particular alkoxy groups that may be mentioned include, for example, methoxy, ethoxy, propoxy, and butoxy.

Unless otherwise specified, cycloalkyl groups as defined herein may, when there is a sufficient number (i.e. a minimum of four) of carbon atoms, be part cyclic/acyclic.

Unless otherwise specified, alkylene groups as defined herein may be straight-chain or, when there is a sufficient number (i.e. a minimum of two) of carbon atoms, be branched.

Unless otherwise stated:

the term "aryl" includes references to 6 to 14-membered carbocyclic groups comprising one, two or three carbocyclic rings, at least one of which rings is fully aromatic; and the point of attachment of aryl groups may be via any atom of the ring system.

However, when aryl groups are bicyclic or tricyclic, they are linked to the rest of the molecule via an aromatic ring. Aryl groups include phenyl, naphthyl and the like.

Unless otherwise specified, the term "halo" includes references to fluoro, chloro, bromo or iodo, in particular, to fluoro, chloro or bromo, especially fluoro or chloro.

Unless otherwise specified, the terms "heteroaryl" and "heteroaromatic" represent, independently upon each occurrence, a 5- to 10-membered heterocyclic group that is fully aromatic, which group contains one or more heteroatoms selected from N, O and S.

Unless otherwise specified, the term "heterocyclyl" specifies, independently upon each occurrence, a 4- to 7-membered heterocyclic ring that is fully saturated or partially unsaturated, which group contains one or more heteroatoms selected from N, O and S.

For the avoidance of doubt, oxo substituents that may be present on heterocyclic (heteroaryl, heteroaromatic and heterocyclyl) groups may be attached to any appropriate atoms in the heterocyclic ring including, where valencies allow, to C-, N- and/or S-atoms within the ring (thereby forming keto, N-oxide, S(O) and/or S(O)$_2$ groups) and/or to any fused benzene or heteroaromatic ring forming part of a heterocyclic group.

Embodiments of the invention that may be mentioned include compounds of formula I in relation to which one or more of the following apply:

(i) X represents chloro or, particularly, fluoro;
(ii) Ak represents $C_{1-4}$ alkyl optionally substituted by one or more fluorine atoms;
(iii) s represents 1;
(iv) A represents S(O) or, particularly, C;
(v) $R^1$ and $R^2$ independently represent H, $C_{1-4}$ alkyl, aryl, heteroaryl or heterocyclyl, which latter four groups are optionally substituted by one or more substituents selected from halo, cyano, oxo, $CO_2H$, $C(O)NR^5R^6$, $S(O)_2R^5$, —$(OCH_2CH_2)_{0-2}OR^5$, heterocyclyl, $C_{1-4}$ alkyl, $C_{2-4}$ alkenyl or $C_{2-4}$ alkynyl, which latter three groups are optionally substituted by one or more halo substituents (e.g. $R^1$ and $R^2$ independently represent H, $C_{1-4}$ alkyl, aryl or heteroaryl, which latter three groups are optionally substituted by one or more substituents selected from halo, $CO_2H$, $C(O)NR^5R^6$, $C_{1-4}$ alkyl, $C_{2-4}$ alkenyl or $C_{2-4}$ alkynyl, which latter three groups are optionally substituted by one or more halo substituents);
(vi) $R^1$ and $R^2$, together with the N-atom to which they are attached, form a 4- to 7-membered heterocyclic group that is fully saturated or partially unsaturated and which heterocyclic group contains one N atom (the atom to which $R^1$ and $R^2$ are attached) and, optionally, one or two further heteroatoms selected from O, S and N, and which heterocyclic group is optionally fused to a benzene or 6-membered heteroaromatic ring, and which heterocyclic group is optionally substituted by one or more substituents selected from halo, hydroxy, oxo, $CO_2H$, $S(O)_2R^5$, $C(O)NR^5R^6$, $C_{1-4}$ alkyl, $C_{1-4}$ alkoxy, phenyl, heteroaryl and heterocyclyl, which latter five groups are optionally substituted by one or more substituents selected from halo, $C_{1-2}$ alkyl, $C_{1-2}$ alkoxy, oxo and hydroxy (e.g. which heterocyclic group is optionally substituted by one or more substituents selected from halo, hydroxy, oxo, $CO_2H$, $C(O)NR^5R^6$, $C_{1-4}$ alkyl, $C_{1-4}$ alkoxy, phenyl, heteroaryl and heterocyclyl, which latter five groups are optionally substituted by one or more substituents selected from halo, $C_{1-2}$ alkyl, $C_{1-2}$ alkoxy, oxo and hydroxy);
(vii) $R^5$ and $R^6$ each independently represent H, $C_{1-4}$ alkyl, —$[CH_2CH_2O]_{1-4}$—$CH_2CH_2$—$R^{6a}$ or —$CH_2$—$[C_{1-3}$ alkylene]-$R^{6a}$;
(viii) $R^5$ and $R^6$, together with the N-atom to which they are attached, form a 4- to 7-membered heterocyclic group that is fully saturated and which heterocyclic group contains one N atom (the atom to which $R^5$ and $R^6$ are attached) and, optionally, a further heteroatom selected from O, S and N, and which heterocyclic group is optionally substituted by one or more substituents selected from halo, hydroxy, oxo, $C_{1-2}$ alkyl and $C_{1-2}$ alkoxy;
(ix) $R^{6a}$ represents $OR^{7a}$, $N(R^{7b})R^{7c}$ or $CO_2H$;
(x) $R^{7a}$ to $R^{7c}$ independently represent H or $C_{1-2}$ alkyl;
(xi) $R^{7b}$ and $R^{7c}$ together with the N-atom to which they are attached, form a 5- or 6-membered heterocyclic group that is fully saturated and which heterocyclic group contains one N atom (the atom to which $R^{7b}$ and $R^{7c}$ are attached) and, optionally, a further heteroatom selected from O, S and N, and which heterocyclic group is optionally substituted by one or more substituents selected from halo, hydroxy, oxo, $C_{1-2}$ alkyl, $C_{1-2}$ alkoxy.

Embodiments of the invention that may be mentioned include those in which the compound of formula I is a compound of formula Ia or Ib,

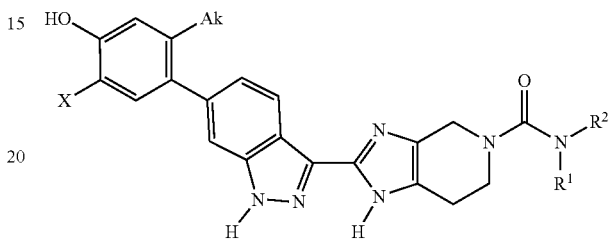

Ia

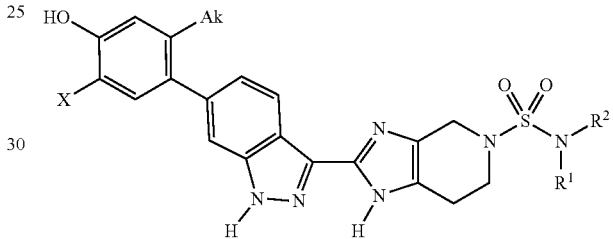

Ib wherein X, Ak, $R^1$ and $R^2$ are as hereinbefore defined.

Embodiments of the invention that may be mentioned include those in which one or more of the following definitions apply to the compounds of formula I, Ia or Ib:

(i) X represents fluoro;
(ii) Ak represents $C_{1-3}$ alkyl, such as ethyl;
(iii) $R^1$ and $R^2$ independently represent H, heterocyclyl, $C_{1-2}$ alkyl or phenyl, which latter two groups are optionally substituted by one or more substituents selected from heterocyclyl, halo, cyano, —$OR^{5a}$ and methyl, which latter group is optionally substituted by one or more halo atoms
(e.g. $R^1$ and $R^2$ independently represent H, $C_{1-2}$ alkyl or phenyl, which latter two groups are optionally substituted by one or more substituents selected from halo and methyl, which latter group is optionally substituted by one or more halo atoms);
(iv) $R^1$ and $R^2$, together with the N-atom to which they are attached, form a 5- or 6-membered heterocyclic group that is fully saturated and which heterocyclic group contains one N atom (the atom to which $R^1$ and $R^2$ are attached) and, optionally, one or two further heteroatoms selected from O, S and N, and which heterocyclic group is optionally fused to a benzene ring, and which heterocyclic group is optionally substituted by one or more substituents selected from halo, oxo, $S(O)_2R^{5b}$, $C_{1-3}$ alkyl, $C_{1-3}$ alkoxy and heterocyclyl (e.g which heterocyclic group is optionally substituted by one or more substituents selected from halo, $C_{1-3}$ alkyl, $C_{1-3}$ alkoxy and heterocyclyl) (e.g. $R^1$ and $R^2$, together with the N-atom to which they are attached, form a heterocyclic group selected from morpholinyl (e.g. morpholin-4-yl), pyrrolidinyl (e.g. pyrrolidin-1-yl), dihydroindole (e.g. 2,3-dihydroindol-1-yl), piperidinyl (e.g. piperidin-1-yl) and piperazinyl (e.g. piperazin-1-yl), which heterocyclic group is optionally substituted by one or more substituents selected from halo, $C_{1-3}$ alkyl, $C_{1-3}$ alkoxy and heterocyclyl);

(v) $R^{5a}$ and $R^{5b}$ independently represent $R^5$ as hereinbefore defined (e.g. $R^{5a}$ represents H or $C_{1-2}$ alkyl, such as methyl, and/or $R^{5b}$ represents $C_{1-2}$ alkyl, such as methyl);

(vi) each heterocyclyl group independently represents a 5- or 6-membered heterocyclic ring that is fully saturated, which group contains one or two heteroatoms selected from N, O and S
(e.g. heterocyclyl represents tetrahydropyranyl (e.g. tetrahydropyran-4-yl), morpholinyl (e.g. morpholin-4-yl), pyrrolidinyl (e.g. pyrrolidin-1-yl) or, particularly, piperidinyl (e.g. piperidin-1-yl).

Other compounds of formula I that may be mentioned include the compounds of the examples described hereinafter. Thus, embodiments of the invention that may be mentioned include those in which the compound of formula I is a compound selected from the list:

(2-(6-(2-ethyl-5-fluoro-4-hydroxyphenyl)-1H-indazol-3-yl)-1,4,6,7-tetrahydro-5H-imidazo[4,5-c]pyridin-5-yl)(morpholino)methanone;
[1,4'-bipiperidin]-1'-yl(2-(6-(2-ethyl-5-fluoro-4-hydroxyphenyl)-1H-indazol-3-yl)-1,4,6,7-tetrahydro-5H-imidazo[4,5-c]pyridin-5-yl)methanone;
(2-(6-(2-ethyl-5-fluoro-4-hydroxyphenyl)-1H-indazol-3-yl)-1,4,6,7-tetrahydro-5H-imidazo[4,5-c]pyridin-5-yl)(indolin-1-Amethanone;
1-ethyl-4-(2-(6-(2-ethyl-5-fluoro-4-hydroxyphenyl)-1H-indazol-3-yl)-4,5,6,7-tetrahydro-1H-imidazo[4,5-c]pyridine-5-carbonyl)piperazine-2,3-dione;
(2-(6-(2-ethyl-5-fluoro-4-hydroxyphenyl)-1H-indazol-3-yl)-1,4,6,7-tetrahydro-5H-imidazo[4,5-c]pyridin-5-yl)(pyrrolidin-1-methanone;
2-(6-(2-ethyl-5-fluoro-4-hydroxyphenyl)-1H-indazol-3-yl)-N-methyl-N-phenyl-1,4,6,7-tetrahydro-5H-imidazo[4,5-c]pyridine-5-carboxamide;
2-(6-(2-ethyl-5-fluoro-4-hydroxyphenyl)-1H-indazol-3-yl)-N-((tetrahydro-2H-pyran-4-yl)methyl)-6,7-dihydro-1H-imidazo[4,5-c]pyridine-5(4H)-carboxamide;
2-(6-(2-ethyl-5-fluoro-4-hydroxyphenyl)-1H-indazol-3-yl)-N-(2-(2-methoxyethoxy)ethyl)-6,7-dihydro-1H-imidazo[4,5-c]pyridine-5(4H)- carboxamide;
2-(6-(2-ethyl-5-fluoro-4-hydroxyphenyl)-1H-indazol-3-yl)-N-(4-(methylsulfonyl)phenyl)-6,7-dihydro-1H-imidazo[4,5-c]pyridine-5(4H)-carboxamide;
N-(3,5-dimethylisoxazol-4-yl)-2-(6-(2-ethyl-5-fluoro-4-hydroxyphenyl)-1H-indazol-3-yl)-6,7-dihydro-1H-imidazo[4,5-c]pyridine-5(4H)- carboxamide;
N-(1,3-dimethyl-2,4-dioxo-1,2,3,4-tetrahydropyrimidin-5-yl)-2-(6-(2-ethyl-5-fluoro-4-hydroxyphenyl)-1H-indazol-3-yl)-6,7-dihydro-1H-imidazo[4,5-c]pyridine-5(4H)-carboxamide;
N-(benzo[c][1,2,5]thiadiazol-4-yl)-2-(6-(2-ethyl-5-fluoro-4-hydroxyphenyl)-1H-indazol-3-yl)-6,7-dihydro-1H-imidazo[4,5-c]pyridine-5(4H)-carboxamide;
2-(6-(2-ethyl-5-fluoro-4-hydroxyphenyl)-1H-indazol-3-yl)-N-phenyl-6,7-dihydro-1H-imidazo[4,5-c]pyridine-5(4H)-carboxamide;
5-ethyl-2-fluoro-4-(3-(5-((4-(methylsulfonyl)piperazin-1-yl)sulfonyl)-4,5,6,7-tetrahydro-1H-imidazo[4,5-c]pyridin-2-yl)-1H-indazol-6-yl)phenol;
N-(2-cyanoethyl)-2-(6-(2-ethyl-5-fluoro-4-hydroxyphenyl)-1H-indazol-3-yl)-N-(2-methoxyethyl)-6,7-dihydro-1H-imidazo[4,5-c]pyridine-5(4H)- sulfonamide;
1-((2-(6-(2-ethyl-5-fluoro-4-hydroxyphenyl)-1H-indazol-3-yl)-6,7-dihydro-1H-imidazo[4,5-c]pyridin-5(4H)-yl)sulfonyl)-N-methylpiperidine-4-carboxamide;
2-(6-(2-ethyl-5-fluoro-4-hydroxyphenyl)-1H-indazol-3-yl)-N-methyl-N-(tetrahydro-2H-pyran-4-yl)-6,7-dihydro-1H-imidazo[4,5-c]pyridine-5(4H)-sulfonamide;
5-ethyl-2-fluoro-4-(3-(5-(pyrrolidin-1-ylsulfonyl)-4,5,6,7-tetrahydro-1H-imidazo[4,5-c]pyridin-2-yl)-1H-indazol-6-yl)phenol;
5-ethyl-2-fluoro-4-(3-(5-(morpholinosulfonyl)-4,5,6,7-tetrahydro-1H-imidazo[4,5-c]pyridin-2-yl)-1H-indazol-6-yl)phenol;
5-ethyl-2-fluoro-4-(3-(5-((4-methylpiperazin-1-yl)sulfonyl)-4,5,6,7-tetrahydro-1H-imidazo[4,5-c]pyridin-2-yl)-1H-indazol-6-yl)phenol;
4-((2-(6-(2-ethyl-5-fluoro-4-hydroxyphenyl)-1H-indazol-3-yl)-6,7-dihydro-1H-imidazo[4,5-c]pyridin-5(4H)-yl)sulfonyl)thiomorpholine 1,1-dioxide;
4-((2-(6-(2-ethyl-5-fluoro-4-hydroxyphenyl)-1H-indazol-3-yl)-6,7-dihydro-1H-imidazo[4,5-c]pyridin-5(4H)-yl)sulfonyl)piperazine-1-carbaldehyde; and
5-ethyl-2-fluoro-4-(3-(5-((4-methoxypiperidin-1-yl)sulfonyl)-4,5,6,7-tetrahydro-1H-imidazo[4,5-c]pyridin-2-yl)-1H-indazol-6-yl)phenol, or a pharmaceutically acceptable salt, solvate or isotopic derivative thereof.

Further embodiments of the invention that may be mentioned include those in which either
(i) the compound of formula I, Ia or Ib represents, or
(ii) the compound of formula I, Ia or Ib is as hereinbefore defined, provided that is does not represent
5-ethyl-2-fluoro-4-(3-(5-((4-(methylsulfonyl)piperazin-1-yl)sulfonyl)-4,5,6,7-tetrahydro-1H-imidazo[4,5-c]pyridin-2-yl)-1H-indazol-6-yl)phenol
or a pharmaceutically acceptable salt, solvate or isotopic derivative thereof.

Examples of salts of compounds of formula I include all pharmaceutically acceptable salts, such as, without limitation, acid addition salts of strong mineral acids such as HCl, $H_2SO_4$ and HBr salts (e.g. HCl or HBr salts) and addition salts of strong organic acids such as methanesulfonic acid.

References herein to a compound of the invention (a compound of formula I) are intended to include references to the compound and to all pharmaceutically acceptable salts, solvates and/or tautomers of said compound, unless the context specifically indicates otherwise. In this respect, solvates that may be mentioned include hydrates.

The compounds of the invention (compounds of formula I) are JAK kinase inhibitors and are therefore useful in medicine, in particular for the treatment of inflammatory diseases. Further aspects of the invention that may be mentioned therefore include the following.

(a) A pharmaceutical formulation comprising a compound of formula I, Ia or Ib, as hereinbefore defined, or pharmaceutically acceptable salt, solvate or isotopic derivative thereof, in admixture with a pharmaceutically acceptable adjuvant, diluent or carrier.

(b) A combination product comprising
(A) a compound of formula I, Ia or Ib, as hereinbefore defined, or pharmaceutically acceptable salt, solvate or isotopic derivative thereof, and (B) another therapeutic agent,
wherein each of components (A) and (B) is formulated in admixture with a pharmaceutically-acceptable adjuvant, diluent or carrier.

In this aspect of the invention, the combination product may be either a single (combination) pharmaceutical formulation or a kit-of-parts.

Thus, this aspect of the invention encompasses a pharmaceutical formulation including a compound of formula I, Ia or Ib, as hereinbefore defined, or pharmaceutically acceptable salt, solvate or isotopic derivative thereof, and another therapeutic agent, in admixture with a pharmaceutically acceptable adjuvant, diluent or carrier (which formulation is hereinafter referred to as a "combined preparation").

It also encompasses a kit of parts comprising components:
(i) a pharmaceutical formulation including a compound of formula I, Ia or Ib, as hereinbefore defined, or pharmaceutically acceptable salt, solvate or isotopic derivative thereof, in admixture with a pharmaceutically acceptable adjuvant, diluent or carrier; and
(ii) a pharmaceutical formulation including another therapeutic agent, in admixture with a pharmaceutically-acceptable adjuvant, diluent or carrier,
which components (i) and (ii) are each provided in a form that is suitable for administration in conjunction with the other.

Component (i) of the kit of parts is thus component (A) above in admixture with a pharmaceutically acceptable adjuvant, diluent or carrier. Similarly, component (ii) is component (B) above in admixture with a pharmaceutically acceptable adjuvant, diluent or carrier.

(c) A process for preparing the pharmaceutical formulation of aspect (a) above, said process comprising the step of admixing the compound of formula I, Ia or Ib, as hereinbefore defined, or pharmaceutically acceptable salt, solvate or isotopic derivative thereof, with a pharmaceutically acceptable adjuvant, diluent or carrier.

Embodiments of this aspect of the invention that may be mentioned include those in which the pharmaceutically acceptable adjuvant, diluent or carrier is a topically acceptable adjuvant, diluent or carrier (and/or wherein the process is for preparing a topical pharmaceutical formulation, i.e. a pharmaceutical formulation that is adapted for topical administration).

(d) A compound of formula I, Ia or Ib, as hereinbefore defined, or pharmaceutically acceptable salt, solvate or isotopic derivative thereof, for use in medicine (or for use as a medicament or as a pharmaceutical).

(e) A compound of formula I, Ia or Ib, as hereinbefore defined, or pharmaceutically acceptable salt, solvate or isotopic derivative thereof, or a pharmaceutical formulation or combination product as defined in connection with aspect (a) or (b) of the invention, for use in the treatment or prevention of an inflammatory disease.

(f) The use of
a compound of formula I, Ia or Ib, as hereinbefore defined, or pharmaceutically acceptable salt, solvate or isotopic derivative thereof, or
a pharmaceutical formulation or combination product as defined in connection with aspect (a) or (b) of the invention,
for the preparation of a medicament for the treatment or prevention of an inflammatory disease.

(g) A method of treating or preventing an inflammatory disease, said method comprising administering to a subject an effective amount of
a compound of formula I, Ia or Ib, as hereinbefore defined, or pharmaceutically acceptable salt, solvate or isotopic derivative thereof, or
a pharmaceutical formulation or combination product as defined in connection with aspect (a) or (b) of the invention.

(h) A method of sensitizing a subject to the anti-inflammatory effects of a corticosteroid, said method comprising administering to the subject an effective amount of
a compound of formula I, Ia or Ib, as hereinbefore defined, or pharmaceutically acceptable salt, solvate or isotopic derivative thereof, or
a pharmaceutical formulation or combination product as defined in connection with aspect (a) or (b) of the invention.

Embodiments of this aspect of the invention that may be mentioned include those in which the subject is one who has become refractory to the anti-inflammatory effects of a corticosteroid.

References herein to "preventing an inflammatory disease" include references to preventing (or reducing the likelihood of) the recurrence of an inflammatory disease in a subject who has previously suffered from such a disease (e.g. a subject who has previously received treatment for that disease, for example treatment according to the method described in (g) above).

Thus, still further aspects of the invention that may be mentioned include the following.

(i) A compound of formula I, Ia or Ib, as hereinbefore defined, or pharmaceutically acceptable salt, solvate or isotopic derivative thereof, or a pharmaceutical formulation or combination product as defined in connection with aspect (a) or (b) of the invention, for use in reducing the likelihood of the recurrence of an inflammatory disease in a subject who has previously received treatment for that disease (e.g. treatment with a compound of formula I, Ia or Ib, as hereinbefore defined, or pharmaceutically acceptable salt, solvate or isotopic derivative thereof, or a pharmaceutical formulation or combination product as defined in connection with aspect (a) or (b) of the invention).

(j) The use of
a compound of formula I, Ia or Ib, as hereinbefore defined, or pharmaceutically acceptable salt, solvate or isotopic derivative thereof, or
a pharmaceutical formulation or combination product as defined in connection with aspect (a) or (b) of the invention,
for the preparation of a medicament for reducing the likelihood of the recurrence of an inflammatory disease in a subject who has previously received treatment for that disease (e.g. treatment with a compound of formula I, Ia or Ib, as hereinbefore defined, or pharmaceutically acceptable salt, solvate or isotopic derivative thereof, or a pharmaceutical formulation or combination product as defined in connection with aspect (a) or (b) of the invention).

(k) A method of reducing the likelihood of the recurrence of an inflammatory disease in a subject who has previously received treatment for that disease (e.g. treatment with a compound of formula I, Ia or Ib, as hereinbefore defined, or pharmaceutically acceptable salt, solvate or isotopic derivative thereof, or a pharmaceutical formulation or combination product as defined in connection with aspect (a) or (b) of the invention), said method comprising administering to said subject an effective amount of a compound of formula I, Ia or Ib, as hereinbefore defined, or pharmaceutically acceptable salt, solvate or isotopic derivative thereof, or a pharmaceutical formulation or combination product as defined in connection with aspect (a) or (b) of the invention.

Formulations

In relation to aspects (a) and (b) above, diluents and carriers that may be mentioned include those suitable for parenteral, oral, topical, mucosal and rectal administration.

The pharmaceutical formulations and combination products of aspects (a) and (b) above may be prepared e.g. for parenteral, subcutaneous, intramuscular, intravenous, intra-articular, intravitreous, periocular, retrobulbar, subconjunctival, sub-Tenon, topical ocular or peri-articular administration, particularly in the form of liquid solutions, emulsions or suspensions; for oral administration, particularly in the form of tablets or capsules, and especially involving technologies aimed at furnishing colon-targeted drug release (Patel, M. M. *Expert Opin. Drug Deliv.* 2011, 8 (10), 1247-1258); for topical e.g. pulmonary or intranasal administration, particularly in the form of powders, nasal drops or aerosols and transdermal administration; for topical ocular administration, particularly in the form of solutions, emulsions, suspensions, ointments, implants/inserts, gels, jellies or liposomal microparticle formulations (Ghate, D.; Edelhauser, H. F. *Expert Opin. Drug Deliv.* 2006, 3 (2), 275-287); for ocular administration, particularly in the form of biodegradable and non-biodegradable implants, liposomes and nanoparticles (Thrimawithana, T. R. et al. *Drug Discov. Today* 2011, 16 (5/6), 270-277); for mucosal administration e.g. to buccal, sublingual or vaginal mucosa, and for rectal administration e.g. in the form of a suppository or enema.

The pharmaceutical formulations and combination products of aspects (a) and (b) above may conveniently be administered in unit dosage form and may be prepared by any of the methods well-known in the pharmaceutical art, for example as described in Remington's Pharmaceutical Sciences, 17th ed., Mack Publishing Company, Easton, Pa., (1985). Formulations for parenteral administration may contain as excipients sterile water or saline, alkylene glycols such as propylene glycol, polyalkylene glycols such as polyethylene glycol, oils of vegetable origin, hydrogenated naphthalenes and the like. Formulations for nasal administration may be solid and may contain excipients, for example, lactose or dextran, or may be aqueous or oily solutions for use in the form of nasal drops or metered sprays. For buccal administration, typical excipients include sugars, calcium stearate, magnesium stearate, pregelatinised starch, and the like.

Pharmaceutical formulations and combination products suitable for oral administration may comprise one or more physiologically compatible carriers and/or excipients and may be in solid or liquid form. Tablets and capsules may be prepared with binding agents, for example, syrup, acacia, gelatin, sorbitol, tragacanth, or poly-vinylpyrrolidone; fillers, such as lactose, sucrose, corn starch, calcium phosphate, sorbitol, or glycine; lubricants, such as magnesium stearate, talc, polyethylene glycol, or silica; and surfactants, such as sodium lauryl sulfate. Liquid compositions may contain conventional additives such as suspending agents, for example sorbitol syrup, methyl cellulose, sugar syrup, gelatin, carboxymethyl-cellulose, or edible fats; emulsifying agents such as lecithin, or acacia; vegetable oils such as almond oil, coconut oil, cod liver oil, or peanut oil; preservatives such as butylated hydroxyanisole (BHA) and butylated hydroxytoluene (BHT). Liquid compositions may be encapsulated in, for example, gelatin to provide a unit dosage form.

Solid oral dosage forms include tablets, two-piece hard shell capsules and soft elastic gelatin (SEG) capsules. Such two-piece hard shell capsules may be made from, for example, gelatin or hydroxylpropyl methylcellulose (HPMC).

A dry shell formulation typically comprises of about 40% to 60% w/w concentration of gelatin, about a 20% to 30% concentration of plasticizer (such as glycerin, sorbitol or propylene glycol) and about a 30% to 40% concentration of water. Other materials such as preservatives, dyes, opacifiers and flavours also may be present. The liquid fill material comprises a solid drug that has been dissolved, solubilized or dispersed (with suspending agents such as beeswax, hydrogenated castor oil or polyethylene glycol 4000) or a liquid drug in vehicles or combinations of vehicles such as mineral oil, vegetable oils, triglycerides, glycols, polyols and surface-active agents.

A compound of the invention may be administered topically (e.g. to the lung, eye or intestines). Thus, embodiments of aspects (a) and (b) above that may be mentioned include pharmaceutical formulations and combination products that are adapted for topical administration. Such formulations include those in which the excipients (including any adjuvant, diluent and/or carrier) are topically acceptable.

Topical administration to the lung may be achieved by use of an aerosol formulation. Aerosol formulations typically comprise the active ingredient suspended or dissolved in a suitable aerosol propellant, such as a chlorofluorocarbon (CFC) or a hydrofluorocarbon (HFC). Suitable CFC propellants include trichloromonofluoromethane (propellant 11), dichlorotetrafluoroethane (propellant 114), and dichlorodifluoromethane (propellant 12). Suitable HFC propellants include tetrafluoroethane (HFC-134a) and heptafluoropropane (HFC-227). The propellant typically comprises 40% to 99.5% e.g. 40% to 90% by weight of the total inhalation composition. The formulation may comprise excipients including co-solvents (e.g. ethanol) and surfactants (e.g. lecithin, sorbitan trioleate and the like). Other possible excipients include polyethylene glycol, polyvinylpyrrolidone, glycerine and the like. Aerosol formulations are packaged in canisters and a suitable dose is delivered by means of a metering valve (e.g. as supplied by Bespak, Valois or 3M or alternatively by Aptar, Coster or Vari).

Topical administration to the lung may also be achieved by use of a non-pressurised formulation such as an aqueous solution or suspension. This may be administered by means of a nebuliser e.g. one that can be hand-held and portable or for home or hospital use (i.e. non-portable). The formulation may comprise excipients such as water, buffers, tonicity adjusting agents, pH adjusting agents, surfactants and co-solvents. Suspension liquid and aerosol formulations (whether pressurised or unpressurised) will typically contain the compound of the invention in finely divided form, for example with a $D_{50}$ of 0.5-10 μm e.g. around 1-5 μm. Particle size distributions may be represented using $D_{10}$, $D_{50}$ and $D_{90}$ values. The $D_{50}$ median value of particle size distributions is defined as the particle size in microns that divides the distribution in half. The measurement derived from laser diffraction is more accurately described as a volume distribution, and consequently the $D_{50}$ value obtained using this procedure is more meaningfully referred to as a $Dv_{50}$ value (median for a volume distribution). As used herein Dv values refer to particle size distributions measured using laser diffraction. Similarly, $D_{10}$ and $D_{90}$ values, used in the context of laser diffraction, are taken to mean $Dv_{10}$ and $Dv_{90}$ values and refer to the particle size whereby 10% of the distribution lies below the $D_{10}$ value, and 90% of the distribution lies below the $D_{90}$ value, respectively.

Topical administration to the lung may also be achieved by use of a dry-powder formulation. A dry powder formulation will contain the compound of the disclosure in finely divided form, typically with a mass mean aerodynamic diameter (MMAD) of 1-10 µm or a $D_{50}$ of 0.5-10 µm e.g. around 1-5 µm. Powders of the compound of the invention in finely divided form may be prepared by a micronization process or similar size reduction process. Micronization may be performed using a jet mill such as those manufactured by Hosokawa Alpine. The resultant particle size distribution may be measured using laser diffraction (e.g. with a Malvern Mastersizer 2000S instrument). The formulation will typically contain a topically acceptable diluent such as lactose, glucose or mannitol (preferably lactose), usually of large particle size e.g. an MMAD of 50 µm or more, e.g. 100 µm or more or a $D_{50}$ of 40-150 µm. As used herein, the term "lactose" refers to a lactose-containing component, including α-lactose monohydrate, β-lactose monohydrate, α-lactose anhydrous, β-lactose anhydrous and amorphous lactose. Lactose components may be processed by micronization, sieving, milling, compression, agglomeration or spray drying. Commercially available forms of lactose in various forms are also encompassed, for example Lactohale® (inhalation grade lactose; DFE Pharma), InhaLac®70 (sieved lactose for dry powder inhaler; Meggle), Pharmatose® (DFE Pharma) and Respitose® (sieved inhalation grade lactose; DFE Pharma) products. In one embodiment, the lactose component is selected from the group consisting of α-lactose monohydrate, β-lactose anhydrous and amorphous lactose. Preferably, the lactose is α-lactose monohydrate.

Dry powder formulations may also contain other excipients such as sodium stearate, calcium stearate or magnesium stearate.

A dry powder formulation is typically delivered using a dry powder inhaler (DPI) device. Examples of dry powder delivery systems include SPINHALER, DISKHALER, TURBOHALER, DISKUS and CLICKHALER. Further examples of dry powder delivery systems include ECLIPSE, NEXT, ROTAHALER, HANDIHALER, AEROLISER, CYCLOHALER, BREEZHALER/NEOHALER, MONODOSE, FLOWCAPS, TWINCAPS, X-CAPS, TURBOSPIN, ELPENHALER, MIATHALER, TWISTHALER, NOVOLIZER, PRESSAIR, ELLIPTA, ORIEL dry powder inhaler, MICRODOSE, PULVINAL, EASYHALER, ULTRAHALER, TAIFUN, PULMOJET, OMNIHALER, GYROHALER, TAPER, CONIX, XCELOVAIR and PROHALER.

In one embodiment a compound of the present invention is provided in a micronized dry powder formulation, for example further comprising lactose of a suitable grade optionally together with magnesium stearate, filled into a single dose device such as AEROLISER or filled into a multi dose device such as DISKUS.

The compounds of the present invention may also be administered rectally, for example in the form of suppositories or enemas, which include aqueous or oily solutions as well as suspensions and emulsions. Such compositions are prepared following standard procedures, well known by those skilled in the art. For example, suppositories can be prepared by mixing the active ingredient with a conventional suppository base such as cocoa butter or other glycerides, e.g. Suppocire. In this case, the drug is mixed with a suitable non-irritating excipient which is solid at ordinary temperatures but liquid at the rectal temperature and will therefore melt in the rectum to release the drug. Such materials are cocoa butter and polyethylene glycols.

Generally, for compositions intended to be administered topically to the eye in the form of eye drops or eye ointments, the total amount of the inhibitor will be about 0.0001 to less than 4.0% (w/w).

Preferably, for topical ocular administration, the compositions administered according to the present invention will be formulated as solutions, suspensions, emulsions and other dosage forms. Aqueous solutions are generally preferred, based on ease of formulation, as well as a patient's ability to administer such compositions easily by means of instilling one to two drops of the solutions in the affected eyes. However, the compositions may also be suspensions, viscous or semi-viscous gels, or other types of solid or semi-solid compositions. Suspensions may be preferred for compounds that are sparingly soluble in water.

The compositions administered according to the present invention may also include various other ingredients, including, but not limited to, tonicity agents, buffers, surfactants, stabilizing polymer, preservatives, co-solvents and viscosity building agents. Preferred pharmaceutical compositions of the present invention include the inhibitor with a tonicity agent and a buffer. The pharmaceutical compositions of the present invention may further optionally include a surfactant and/or a palliative agent and/or a stabilizing polymer.

Various tonicity agents may be employed to adjust the tonicity of the composition, preferably to that of natural tears for ophthalmic compositions. For example, sodium chloride, potassium chloride, magnesium chloride, calcium chloride, simple sugars, such as dextrose, fructose, galactose, and/or simply polyols, such as the sugar alcohols mannitol, sorbitol, xylitol, lactitol, isomaltitol, maltitol, and hydrogenated starch hydrolysates may be added to the composition to approximate physiological tonicity. Such an amount of tonicity agent will vary, depending on the particular agent to be added. In general, however, the compositions will have a tonicity agent in an amount sufficient to cause the final composition to have an ophthalmically acceptable osmolality (generally about 150-450 mOsm, preferably 250-350 mOsm and most preferably at approximately 290 mOsm). In general, the tonicity agents of the invention will present in the range of 2 to 5% w/w. Preferred tonicity agents of the invention include the simple sugars or the sugar alcohols, such as D-mannitol.

An appropriate buffer system (e.g. sodium phosphate, sodium acetate, sodium citrate, sodium borate or boric acid) may be added to the compositions to prevent pH drift under storage conditions. The particular concentration will vary, depending on the agent employed. Preferably however, the buffer will be chosen to maintain a target pH within the range of pH 5 to 8.

Surfactants may optionally be employed to deliver higher concentrations of inhibitor. The surfactants function to solubilise the inhibitor and stabilise colloid dispersion, such as micellar solution, microemulsion, emulsion and suspension. Examples of surfactants which may optionally be used include polysorbate, poloxamer, polyoxyl 40 stearate, polyoxyl castor oil, tyloxapol, triton, and sorbitan monolaurate. Preferred surfactants to be employed in the invention have a hydrophile/lipophile/balance "HLB" in the range of 12.4 to 13.2 and are acceptable for ophthalmic use, such as TritonX114 and tyloxapol.

Additional agents that may be added to the ophthalmic compositions of the present invention are demulcents which function as a stabilising polymer. The stabilizing polymer should be an ionic/charged example with precedence for topical ocular use, more specifically, a polymer that carries negative charge on its surface that can exhibit a zeta-potential of (−)10-50 mV for physical stability and capable of making a dispersion in water (i.e. water soluble). A preferred stabilising polymer of the invention would be polyelectrolyte, or polyelectrolytes if more than one, from the family of cross-linked polyacrylates, such as carbomers, polycarbophil and Pemulen(R), specifically Carbomer 974p (polyacrylic acid), at 0.1-0.5% w/w.

Other compounds may also be added to the ophthalmic compositions of the present invention to increase the viscosity of the carrier. Examples of viscosity enhancing agents include, but are not limited to: polysaccharides, such as hyaluronic acid and its salts, chondroitin sulfate and its salts, dextrans, various polymers of the cellulose family, vinyl polymers and acrylic acid polymers.

Topical ophthalmic products are typically packaged in multidose form. Preservatives are thus required to prevent microbial contamination during use. Suitable preservatives include: benzalkonium chloride, chlorobutanol, benzododecinium bromide, methyl paraben, propyl paraben, phenylethyl alcohol, edentate disodium, sorbic acid, polyquaternium-1, or other agents known to those skilled in the art. Such preservatives are typically employed at a level of from 0.001 to 1.0% w/v. Unit dose compositions of the present invention will be sterile, but typically unpreserved. Such compositions, therefore, generally will not contain preservatives.

The medical practitioner, or other skilled person, will be able to determine a suitable dosage for the compounds of the invention, and hence the amount of the compound of the invention that should be included in any particular pharmaceutical formulation (whether in unit dosage form or otherwise).

Embodiments of the invention that may be mentioned in connection with the combination products described at (b) above include those in which the other therapeutic agent is one or more therapeutic agents that are known by those skilled in the art to be suitable for treating inflammatory diseases (e.g. the specific diseases mentioned below).

For example, for the treatment of respiratory disorders (such as COPD or asthma), the other therapeutic agent is one or more agents selected from the list comprising:
  steroids (e.g. budesonide, beclomethasone dipropionate, fluticasone propionate, mometasone furoate, fluticasone furoate; a further example is ciclesonide);
  beta agonists, particularly beta2 agonists (e.g. terbutaline, salbutamol, salmeterol, formoterol; further examples are vilanterol, olodaterol, reproterol and fenoterol); and
  xanthines (e.g. theophylline).

For example, for the treatment of respiratory disorders (such as COPD or asthma), the other therapeutic agent is one or more agents selected from the list comprising:
  muscarinic antagonists (e.g. tiotropium, umeclidinium, glycopyrronium, aclidinium and daratropium, any of these for example as the bromide salt); and
  phosphodiesterase inhibitors.

Further, for the treatment of gastrointestinal disorders (such as Crohn's disease or ulcerative colitis), the other therapeutic agent may be, for example, one or more agents selected from the list comprising:
  5-aminosalicylic acid, or a prodrug thereof (such as sulfasalazine, olsalazine or balsalazide);
  corticosteroids (e.g. prednisolone, methylprednisolone, or budesonide); immunosuppressants (e.g. cyclosporin, tacrolimus, methotrexate, azathioprine or 6-mercaptopurine);
  anti-TNFα antibodies (e.g. infliximab, adalimumab, certolizumab pegol or golimurnab);
  anti-IL12/IL23 antibodies (e.g. ustekinumab) or small molecule IL12/IL23 inhibitors (e.g. apilimod);
  anti-α467 antibodies (e.g. vedolizumab);
  toll-like receptor (TLR) blockers (e.g. BL-7040; Avecia (Cambridge, UK));
  MAdCAM-1 blockers (e.g. PF-00547659);
  antibodies against the cell adhesion molecule α4-integrin (e.g. natalizumab);
  antibodies against the IL2 receptor a subunit (e.g. daclizumab or basiliximab);
  anti-Smad7 antibodies (e.g. mongersen (GED0301; all-P-ambo-2'-deoxy-P-thioguanylyl-(3'→5')-P-thiothymidylyl-(3'→5')-2'-deoxy-5-methyl-P-thiocytidylyl-(3'→5)-2'-deoxy-P-thioguanylyl-(3'→5)-2'-deoxy-P-thiocytidylyl-(3'→5')-2'-deoxy-P-thiocytidylyl-(3'→5')-2'-deoxy-P-thiocytidylyl-(3'→5')-2'-deoxy-P-thiocytidylyl-(3'→5')-P-thiothymidylyl-(3'→5')-P-thiothymidylyl-(3'→5')-2'-deoxy-Pthiocytidylyl-(3'→5')-P-thiothymidylyl-(3'→5)-2'-deoxy-P-thiocytidylyl-(3'→5)-2'-deoxy-P-thiocytidylyl-(3'→5)-2'-deoxy-P-thiocytidylyl-(3'→5')-2'-deoxy-5-methyl-P-thiocytidylyl-(3'→5')-2'-deoxy-Pthioguanylyl-(3'→5)-2'-deoxy-P-thiocytidylyl-(3'→5')-2'-deoxy-Pthioadenylyl-(3→5)-2'-deoxy-P-thioguanylyl-(3'→5')-2'-deoxycytidine));
  sphingosine 1-phosphate receptor 1 (S1P1) modulators (e.g. ozanimod ((S)-5-(3-(1-((2-hydroxyethyl)amino)-2,3-dihydro-1H-inden-4-yl)-1,2,4-oxadiazol-5-yl)-2-isopropoxybenzonitrile), amiselimod (MT1303; 2-amino-2-{2-[4-(heptyloxy)-3-(trifluoromethyl)phenyl]ethyl}propane-1,3-diol) or APD334 (2-[7-[4-cyclopentyl-3-(trifluoromethyl)benzyloxy]-1,2,3,4-tetrahydrocyclopenta[b]indol-3(R)-yl]acetic acid));
  STAT3 inhibitors (e.g. TAK-114; (3E)-1-methyl-3-(2-oxo-1H-indol-3-ylidene)indol-2-one);
  Narrow spectrum kinase inhibitors (e.g., TOP1288);
  receptor-interacting protein-1 (RIP1) kinase inhibitors (e.g. GSK2982772);
  Syk inhibitors and prodrugs thereof (e.g. fostamatinib and R-406);
  Phosphodiesterase-4 inhibitors (e.g. tetomilast);
  HMPL-004;
  probiotics;
  microbiome modulators (e.g. SGM1019);
  Dersalazine;
  semapimod/CPSI-2364; and
  protein kinase C inhibitors (e.g. AEB-071)

For the treatment of eye disorders (such as uveitis and keratoconjunctivitis sicca (dry eye)), the other therapeutic agent may be, for example, one or more agents selected from the list comprising:

corticosteroids (e.g. dexamethasone, prednisolone, triamcinolone acetonide, difluprednate or fluocinolone acetonide);
glucocorticoid agonists (e.g. mapracorat);
immunosuppressants (e.g. cyclosporin, voclosporin, azathioprine, methotrexate, mycophenolate mofetil or tacrolimus);
anti-TNFα antibodies (e.g. infliximab, adalimumab, certolizumab pegol, ESBA-105 or golimumab);
anti-IL-17A antibodies (e.g. secukinumab);
mTOR inhibitors (e.g. sirolimus);
VGX-1027;
adenosine A3 receptor agonists (e.g. CF-101);
lifitegrast;
Narrow spectrum kinase inhibitors (e.g., TOP1630);
IL1 blockers (e.g. EBI-005; Hou et al. *PNAS* 2013, 110(10), 3913-3918);
RGN-259 (Thymosin 84);
SI-614;
OTX-101;
JNK inhibitors (e.g. XG-104);
MAP kinase signalling inhibitors (e.g. DA-6034; {[2-(3,4-dimethoxyphenyl)-5-methoxy-4-oxochromen-7-yl]oxy}acetic acid);
mucin stimulators (e.g. rebamipide; 2-[(4-chlorobenzoyl)amino]-3-(2-oxo-1H-quinolin-4-yl)propanoic acid);
MIM-D3 (Tavilermide; see, for example, US 2013/0345395); and
protein kinase C inhibitors (e.g. AEB-071).

Medical Uses

The compounds of the invention may be used as monotherapies for inflammatory diseases, or in combination therapies for such diseases.

Thus, embodiments of aspects (e) to (g) above that may be mentioned include those in which the compound of formula I, Ia or Ib (or pharmaceutically acceptable salt, solvate or isotopic derivative thereof) is the sole pharmacologically active ingredient utilised in the treatment.

However, in other embodiments of aspects (e) to (g) above, the compound of formula I, Ia or Ib (or pharmaceutically acceptable salt, solvate or isotopic derivative thereof) is administered to a subject who is also administered one or more other therapeutic agents (e.g. wherein the one or more other therapeutic agents are as defined above in connection with combination products).

When used herein, the term "inflammatory disease" specifically includes references to any one or more of the following:

(i) lung diseases or disorders having an inflammatory component, such as cystic fibrosis, pulmonary hypertension, lung sarcoidosis, idiopathic pulmonary fibrosis or, particularly, COPD (including chronic bronchitis and emphysema), asthma or paediatric asthma;
(ii) skin diseases or disorders having an inflammatory component, such as atopic dermatitis, allergic dermatitis, contact dermatitis or psoriasis;
(iii) nasal diseases or disorders having an inflammatory component, such as allergic rhinitis, rhinitis or sinusitis;
(iv) eye diseases or disorders having an inflammatory component, such as conjunctivitis, allergic conjunctivitis, glaucoma, diabetic retinopathy, macular oedema (including diabetic macular oedema), central retinal vein occlusion (CRVO), dry and/or wet age related macular degeneration (AMD), post-operative cataract inflammation, or, particularly, keratoconjunctivitis sicca (dry eye, also known as xerophthalmia), uveitis (including posterior, anterior and pan uveitis), corneal graft and limbal cell transplant rejection; and
(v) gastrointestinal diseases or disorders having an inflammatory component, such as gluten sensitive enteropathy (coeliac disease), eosinophilic esophagitis, intestinal graft versus host disease or, particularly, Crohn's disease or ulcerative colitis.

References herein to diseases having an inflammatory component include references to diseases that involve inflammation, whether or not there are other (non-inflammatory) symptoms or consequences of the disease.

According to a further aspect of the invention there is provided a process for the preparation of a compound of formula I, which process comprises:

(a) reaction of a compound of formula II,

with a compound of formula III,

wherein one of $Z^1$ and $Z^2$ is a structural fragment of formula IV,

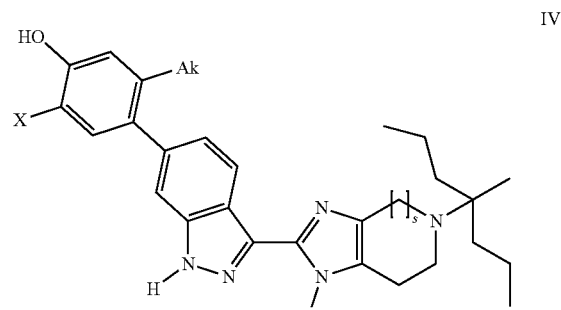

and the other of $Z^1$ and $Z^2$ is a structural fragment of formula V,

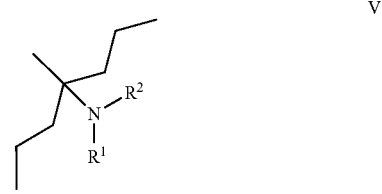

where X, Ak, s, A, $R^1$ and $R^2$ are as hereinbefore defined and LG represents a leaving group (e.g., halogen [Wang, G. T., et al. *Tetrahedron Lett.* 1997, 38, 1895-1898; Krasavin, M., et al. *Bioorg. Med. Chem. Lett.* 2014, 24, 4477-4481; Tung, R. D., et al. U.S. Pat. No. 5,783,701], aryloxy [Mehrotra, M. M., et al. *Bioorg. Med. Chem. Lett.* 2002, 12, 1103-1107; Venier, O., et al. *Bioorg. Med. Chem. Lett.* 2011, 21, 2244-2251], imidazolyl [Velavan, A.; Sumathi, S.; Balasubramanian, K. K. *Org. Biomol. Chem.* 2012, 10, 6420-6431] or imidazolium [formed by N-alkylation of the corresponding imidazole: Grzyb, J. A., Batey, R. A. *Tetrahedron Lett.* 2008, 49, 5279-5282; Eibl, C., et al. *Bioorg. Med. Chem.* 2013, 21, 7283-7308]), for example under conditions known to those skilled in the art, such as in the presence of a suitable organic solvent (e.g., an aprotic solvent such as dichloromethane, acetonitrile, THF, NMP, or mixtures thereof) and a base (e.g., DIPEA or TEA) at room temperature, or optionally at elevated temperatures of up to 50° C.;

(b) for compounds of formula I in which A is C and $R^1$ is H, reaction of an amine of formula II, where $Z^1$ represents a structural fragment of formula IV, with an isocyanate of formula VI,

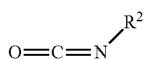
VI where $R^2$ is as hereinbefore defined, for example under conditions known to those skilled in the art (see, for example, Vinaya, K., et al. *Eur. J. Med. Chem.* 2009, 44, 3158-3165; Auberson, Y. P., et al. *ChemMedChem* 2014, 9, 1683-1696; Kusumi, K., et al. *Bioorg. Med. Chem. Lett.* 2015, 25, 1479-1482), such as in the presence of a suitable organic solvent (e.g., an aprotic solvent such as dichloromethane, acetonitrile, THF, NMP, or mixtures thereof) and, optionally, a base (e.g., DIPEA or TEA) at temperatures ranging from 0 to 50° C.;

(c) deprotection of an protected derivative of a compound of formula I, under conditions known to those skilled in the art, wherein the protected derivative bears a protecting group on an O- or N-atom of the compound of formula I (and, for the avoidance of doubt, a protected derivative of one compound of formula I may or may not represent another compound of formula I).

Examples of protected derivatives of compounds of formula I include those where:
- an O-atom is protected with a benzyl group, which benzyl group may be removed by hydrogenation, for example in the presence of a palladium catalyst (such as Pd/C);
- an O-atom of an acid (e.g. a carboxylic acid) is protected with an alkyl group (such as methyl, ethyl or tert-butyl), which alkyl group may be removed by either basic hydrolysis (e.g. for methyl or ethyl groups, by a hydrolysis reaction using an alkali metal hydroxide such as sodium hydroxide) or acid hydrolysis (e.g. for a tert-butyl group, by a hydrolysis reaction using an acid such as trifluoroacetic acid);
- an N-atom of an amine is protected with a carbamate group, such as a benzyl or tert-butyl carbamate, which groups may be removed under similar conditions to those used to remove benzyl or tert-butyl groups from O-atoms.

Compounds of formula III may be made through reaction of a compound of formula VII,

VII with a compound of formula VIII,

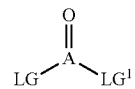
VIII where $Z^2$, A and LG are as hereinbefore defined and $LG^1$ either represents LG or a leaving group that is displaced in preference to LG. Thus, compounds of formula VIII include reactants such as phosgene, diphosgene, triphosgene, sulfuryl chloride, carbonyldiimidazole (CDI), phenyl chloroformate and 4-nitrophenyl chloroformate. The reaction of VII with VIII is typically carried out in the presence of an aprotic solvent (e.g., dichloromethane or THF) and a base (e.g., DIPEA or TEA) at temperatures ranging from 0 to 65° C.

The aspects of the invention described herein (e.g. the above-mentioned compounds, combinations, methods and uses) may have the advantage that, in the treatment of the conditions described herein, they may be more convenient for the physician and/or patient than, be more efficacious than, be less toxic than, have better selectivity over, have a broader range of activity than, be more potent than, produce fewer side effects than, have a better pharmacokinetic and/or pharmacodynamic profile than, have more suitable solid state morphology than, have better long term stability than, or may have other useful pharmacological properties over similar compounds, combinations, methods (treatments) or uses known in the prior art for use in the treatment of those conditions or otherwise.

The compounds of the invention may additionally (or alternatively):
- exhibit a long duration of action and/or persistence of action (e.g. in comparison to the Reference Compound);
- be more potent in biochemical JAK enzyme assays (e.g. in comparison to the Reference Compound);
- exhibit lower $IC_{50}$ values in cellular assays evaluating cytokine release (e.g. in comparison to the Reference Compound);
- produce lower systemic concentrations following oral dosing (e.g. in comparison to the Reference Compound);
- maintain a relatively high local drug concentration between doses (e.g. a high local concentration relative to other previously disclosed JAK inhibitors);
- exhibit properties that are particularly suited to topical/local administration (e.g. following topical/local administration, the generation of high target tissue concentrations but low plasma concentrations of the compounds of formula (I) and/or rapid clearance of the compounds of formula (I) from plasma, for example as a result of high renal or hepatic extraction);
- display reduced cytotoxicities (e.g. in comparison to the Reference Compound); and/or
- exhibit enhanced solubilities (e.g. in comparison to the Reference Compound) in biologically-relevant media, for example, in fasted-state simulated colonic fluid (FaSSCoF; Vertzoni, M., et al. *Pharm. Res.* 2010, 27, 2187-2196).

EXPERIMENTAL SECTION

Abbreviations used herein are defined below. Any abbreviations not defined are intended to convey their generally accepted meaning.

Chemistry Examples

General Procedures

All starting materials and solvents were obtained either from commercial sources or prepared according to the literature citation. Unless otherwise stated, all reactions were stirred. Organic solutions were routinely dried over anhydrous magnesium sulfate.

Preparative Reverse Phase High Performance Liquid Chromatography

Performed using UV detection at 210-400 nm with a Waters X-Bridge Prep-C18, 5 μm, 19×50 mm column eluting with a H2O-MeCN gradient containing 0.1% ammonium bicarbonate over 10 min.

Analytical Methods

Reverse Phase High Performance Liquid Chromatography

Method 1: Agilent Infinity, X-Select, Waters X-Select C18, 2.5 μm (4.6×30 mm) at 40° C.; flow rate 2.5-4.5 mL min$^{-1}$ eluted with a H$_2$O-MeCN gradient containing 0.1% v/v formic acid over 4 min employing UV detection at 254 nm. Gradient information: 0-3.00 min, ramped from 95% H$_2$O-5% MeCN to 5% H$_2$O-95% MeCN; 3.00-3.01 min, held at 5% H$_2$O-95% MeCN, flow rate increased to 4.5 mL min$^{-1}$; 3.01-3.50 min, held at 5% H$_2$O-95% MeCN; 3.50-3.60 min, returned to 95% H$_2$O-5% MeCN, flow rate reduced to 3.50 mL min$^{-1}$; 3.60-3.90 min, held at 95% H$_2$O-5% MeCN; 3.90-4.00 min, held at 95% H$_2$O-5% MeCN, flow rate reduced to 2.5 mL min$^{-1}$.

Method 2: Waters Acquity UPLC C18, 1.7 μm (2.1×50 mm) at 40° C.; inject volume 2 μL; flow rate 0.77 mL min$^{-1}$ eluted with a H$_2$O-MeCN gradient containing 10 mM ammonium bicarbonate over 3 min employing UV detection at 210-400 nm. Gradient information: 0-0.11 min, held at 95% H$_2$O-5% MeCN; 0.11-2.15 min, ramped from 95% H$_2$O-5% MeCN to 5% H$_2$O-95% MeCN; 2.15-2.49 min, held at 5% H$_2$O-95% MeCN; 2.49-2.56 min, returned to 95% H$_2$O-5% MeCN; 2.56-3.00 min, held at 95% H$_2$O-5% MeCN.

$^1$H NMR Spectroscopy $^1$H NMR spectra were acquired on a Bruker Avance III spectrometer at 400 MHz using residual undeuterated solvent as reference and unless specified otherwise were run in DMSO-d$_6$.

Preparation of Compounds of the Invention

Example 1

(2-(6-(2-Ethyl-5-fluoro-4-hydroxyphenyl)-1H-indazol-3-yl)-1,4,6,7-tetrahydro-5H-imidazo[4,5-c]pyridin-5-yl)(morpholino)methanone

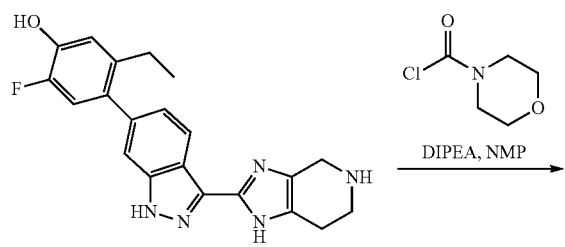

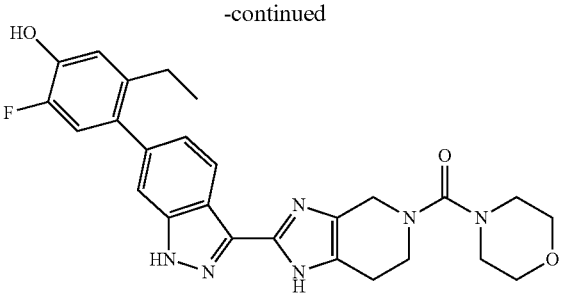

A solution of 5-ethyl-2-fluoro-4-(3-(4,5,6,7-tetrahydro-1H-imidazo[4,5-c]pyridin-2-yl)-1H-indazol-6-yl)phenol.2HCl (Coe, J. W., et al. WO2013/014567, 31 Jan. 2013; 100 mg, 0.265 mmol) in NMP (2 mL) was added to morpholine-4-carbonyl chloride (20.5 mg, 0.265 mmol), followed by DIPEA (185 μL, 1.06 mmol). The solution was stirred at rt for 18 h. The reaction mixture was filtered and then purified by preparative HPLC (Waters, Basic (0.1% Ammonium Bicarbonate), Basic, Waters X-Bridge Prep-C18, 5 μm, 19×50 mm column, 10-40% MeCN in Water) to afford the title compound (43.7 mg).

$^1$H NMR (400 MHz, DMSO-d$_6$) δ: 13.21 (s, 1H), 12.47 and 12.38 (2×s, 1H), 9.84 (s, 1H), 8.32 (d, 1H), 7.38 (t, 1H), 7.11 (dd, 1H), 7.03 (d, 1H), 6.92 (d, 1H), 4.31 (s, 2H), 3.69-3.57 (m, 4H), 3.52 (t, 2H), 3.25-3.14 (m, 4H), 2.80-2.67 (m, 2H), 2.49-2.45 (assume 2H, obscured by solvent), 1.02 (t, 3H).

LCMS m/z 491.4 (M+H)$^+$ (ES$^+$)

Example 2

The following compounds were prepared by methods analogous to those described above for Example 1.

(a) [1,4'-bipiperidin]-1'-yl(2-(6-(2-ethyl-5-fluoro-4-hydroxyphenyl)-1H-indazol-3-yl)-1,4,6,7-tetrahydro-5H-imidazo[4,5-c]pyridin-5-yl)methanone

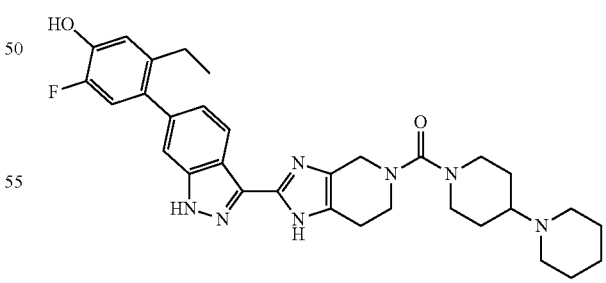

$^1$H NMR (400 MHz, DMSO-d$_6$) δ: 13.21 (s, 1H), 12.46 and 12.36 (2×s, 1H), 9.86 (s, 1H), 8.32 (d, 1H), 7.38 (t, 1H), 7.10 (dd, 1H), 7.03 (d, 1H), 6.92 (d, 1H), 4.27 (s, 2H), 3.72-3.58 (m, 2H), 3.48 (t, 2H), 2.81-2.65 (m, 4H), 2.49-2.32 (m, 7H), 1.71 (d, 2H), 1.54-1.32 (m, 8H), 1.02 (t, 3H).

LCMS m/z 572.5 (M+H)$^+$ (ES$^+$)

(b) (2-(6-(2-ethyl-5-fluoro-4-hydroxyphenyl)-1H-indazol-3-yl)-1,4,6,7-tetrahydro-5H-imidazo[4,5-c]pyridin-5-yl)(indolin-1-yl)methanone

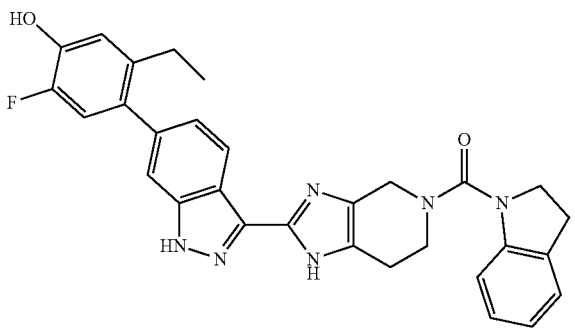 [SMILES: CCc1cc(O)c(F)cc1-c1ccc2c(-c3nc4c([nH]3)CCN(C(=O)N3CCc5ccccc53)C4)n[nH]c2c1]

$^1$H NMR (400 MHz, DMSO-d$_6$) δ: 13.21 (s, 1H), 12.51 and 12.34 (2×s, 1H), 9.84 (s, 1H), 8.29 and 8.33 (2×d, 1H), 7.37 (s, 1H), 7.22 (d, 1H), 7.18-6.99 (m, 4H), 6.94-6.85 (m, 2H), 4.38 and 4.42 (2×s, 2H), 3.89 (t, 2H), 3.67 (t, 2H), 3.03 (t, 2H), 2.85-2.75 (m, 2H), 2.49-2.42 (m, 2H), 1.07-0.97 (m, 3H).
LCMS m/z 523.4 (M+H)$^+$ (ES$^+$)

(c) 1-ethyl-4-(2-(6-(2-ethyl-5-fluoro-4-hydroxyphenyl)-1H-indazol-3-yl)-4,5,6,7-tetrahydro-1H-imidazo[4,5-c]pyridine-5-carbonyl)piperazine-2,3-dione

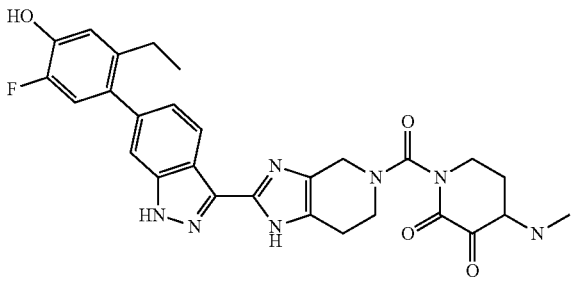 [SMILES: CCc1cc(O)c(F)cc1-c1ccc2c(-c3nc4c([nH]3)CCN(C(=O)N3CCC(NC)C(=O)C3=O)C4)n[nH]c2c1]

$^1$H NMR (400 MHz, DMSO-d$_6$) δ: 13.22 (s, 1H), 12.53 and 12.28 (2×s, 1H), 9.84 (s, 1H), 8.43-8.17 (m, 1H), 7.37 (t, 1H), 7.15-6.98 (m, 2H), 6.91 (d, 1H), 4.69-4.21 (m, 3H), 3.96-3.36 (m, 9H), 2.74 (s, 2H), 1.12 (t, 3H), 1.02 (t, 3H).
LCMS m/z 546.5 (M+H)$^+$ (ES$^+$)

(d) (2-(6-(2-ethyl-5-fluoro-4-hydroxyphenyl)-1H-indazol-3-yl)-1,4,6,7-tetrahydro-5H-imidazo[4,5-c]pyridin-5-yl)(pyrrolidin-1-yl)methanone

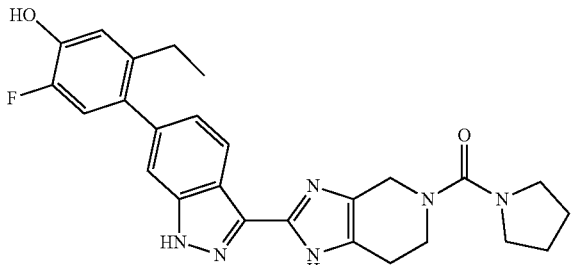

$^1$H NMR (400 MHz, DMSO-d$_6$) δ: 13.20 (s, 1H), 12.44 and 12.37 (2×s, 1H), 9.84 (s, 1H), 8.37-8.28 (m, 1H), 7.40-7.35 (m, 1H), 7.11 (dd, 1H), 7.03 (d, 1H), 6.92 (d, 1H), 4.27 (s, 2H), 3.56-3.48 (m, 2H), 3.38-3.29 (assume 4H, obscured by solvent), 2.77-2.66 (m, 2H), 2.50-2.45 (assume 2H, obscured by solvent), 1.84-1.73 (m, 4H), 1.02 (t, 3H).
LCMS m/z 475.4 (M+H)$^+$ (ES$^+$)

(e) 2-(6-(2-ethyl-5-fluoro-4-hydroxyphenyl)-1H-indazol-3-yl)-N-methyl-N-phenyl-1,4,6,7-tetrahydro-5H-imidazo[4,5-c]pyridine-5-carboxamide

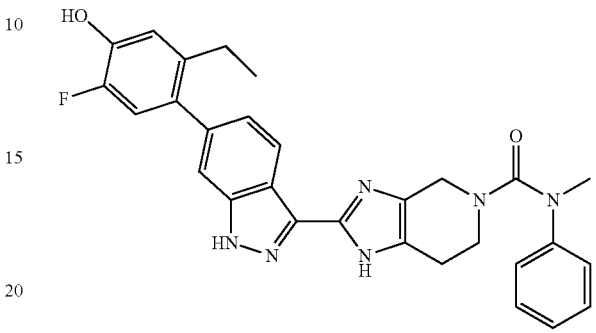

$^1$H NMR (400 MHz, DMSO-d$_6$) δ: 13.18 (s, 1H), 12.40 and 12.30 (2×s, 1H), 8.24 and 8.27 (2×dd, 1H), 7.45-7.32 (m, 3H), 7.24-7.19 (m, 2H), 7.16 (tt, 1H), 7.10-7.04 (m, 1H), 7.01 (d, 1H), 6.91 (d, 1H), 4.06 and 4.20 (2×s, 2H), 3.59-3.44 (m, 2H), 3.14 (s, 3H), 2.49-2.41 (assume 4H, obscured by solvent), 2.36-2.28 (m, 1H), 1.01 (t, 3H).
LCMS m/z 511.4 (M+H)$^+$ (ES$^+$)

Example 3

2-(6-(2-Ethyl-5-fluoro-4-hydroxyphenyl)-1H-indazol-3-yl)-N-((tetrahydro-2H-byran-4-yl)methyl)-6,7-dihydro-1H-imidazo[4,5-c]pyridine-5(4)- carboxamide

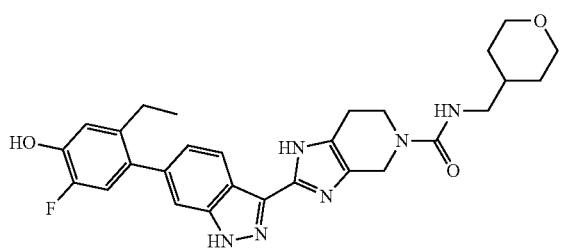 [SMILES: CCc1cc(O)c(F)cc1-c1ccc2c(-c3nc4c([nH]3)CCN(C(=O)NCC3CCOCC3)C4)n[nH]c2c1]

To a stirred solution of 5-ethyl-2-fluoro-4-(3-(4,5,6,7-tetrahydro-1H-imidazo[4,5-c]pyridin-2-yl)-1H-indazol-6-yl)phenol dihydrochloride (50 mg, 0.111 mmol) and DIPEA (97 μL, 0.555 mmol) in DMF (1 mL) was added 4-(isocyanatomethyl)tetrahydro-2H-pyran (17.24 mg, 0.122 mmol). The resulting solution was stirred at rt for 16 h. The reaction mixture was purified by preparative HPLC (Waters, Basic (0.1% Ammonium Bicarbonate), Basic, Waters X-Bridge Prep-C18, 5 μm, 19×50 mm column, 10-40% MeCN in Water) to afford the title compound (23 mg) as a white solid.
$^1$H NMR (400 MHz, DMSO-d$_6$) δ: 13.21 (s, 1H), 12.44 (s, 1H), 9.89 (s, 1H), 8.31 (dd, 1H), 7.37 (s, 1H), 7.10 (dd, 1H), 7.03 (d, 1H), 6.91 (d, 1H), (2×t, 6.74 and 6.65, 1H), 4.49-4.34 (m, 2H), 3.82 (dd, 2H), 3.71-3.59 (m, 2H), 3.23 (p, 2H), 2.95 (t, 2H), 2.68-2.58 (m, 2H), 1.75-1.61 (m, 1H), 1.55 (d, 2H), 1.11 (qd, 2H), 1.01 (t, 3H). 2H under DMSO peak.
LCMS m/z 519 (M+H)$^+$ (ES$^+$)

Example 4

The following compounds were prepared by methods analogous to those described above for Example 3.

(a) 2-(6-(2-ethyl-5-fluoro-4-hydroxyphenyl)-1H-indazol-3-yl)-N-(2-(2-methoxyethoxy)ethyl)-6,7-dihydro-1H-imidazo[4,5-c]pyridine-5(4H)-carboxamide

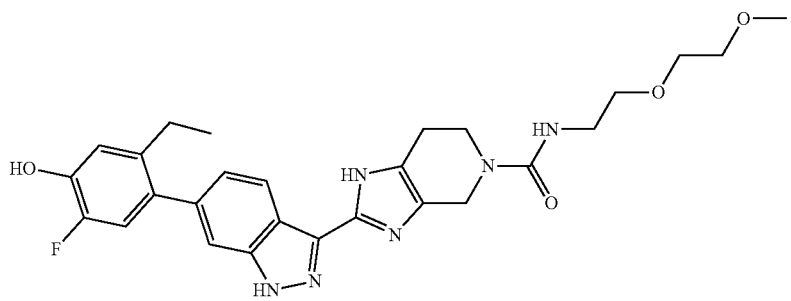 [SMILES: CCc1cc(O)c(F)cc1-c1ccc2c(-c3nc4c([nH]3)CCN(C(=O)NCCOCCOC)C4)n[nH]c2c1]

$^1$H NMR (400 MHz, DMSO-d$_6$) δ: 13.21 (s, 1H), 12.45 (s, 1H), 9.87 (s, 1H), 8.33 (dd, 1H), 7.38 (s, 1H), 7.11 (dd, 1H), 7.03 (d, 1H), 6.92 (d, 1H), 6.72 (dt, 1H), 4.49-4.34 (m, 2H), 3.72-3.60 (m, 2H), 3.54-3.49 (m, 2H), 3.45-3.39 (m, 4H), 3.24 (s, 3H), 3.23-3.17 (m, 2H), 2.70-2.58 (m, 2H), 1.02 (t, 3H). 2H under DMSO peak.
LCMS m/z 523 (M+H)$^+$ (ES$^+$)

(b) 2-(6-(2-ethyl-5-fluoro-4-hydroxyphenyl)-1H-indazol-3-yl)-N-(4-(methylsulfonyl)phenyl)-6,7-dihydro-1H-imidazo[4,5-c]pyridine-5(4H)-carboxamide

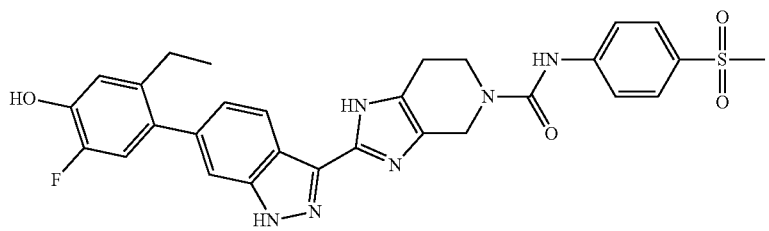 [SMILES: CCc1cc(O)c(F)cc1-c1ccc2c(-c3nc4c([nH]3)CCN(C(=O)Nc3ccc(S(C)(=O)=O)cc3)C4)n[nH]c2c1]

$^1$H NMR (400 MHz, DMSO-d$_6$) δ: 13.26 (s, 1H), 12.54 (s, 1H), 9.87 (s, 1H), (2×s, 9.26 and 9.15, 1H), 8.33 (d, 1H), 7.84-7.68 (m, 4H), 7.39 (s, 1H), 7.11 (dd, 1H), 7.03 (d, 1H), 6.92 (d, 1H), 4.63 (s, 2H), 3.88-3.78 (m, 2H), 3.15 (s, 3H), 2.80-2.72 (m, 2H), 1.02 (t, 3H). 2H under DMSO peak.
LCMS m/z 575 (M+H)$^+$ (ES$^+$)

(c) N-(3,5-dimethylisoxazol-4-yl)-2-(6-(2-ethyl-5-fluoro-4-hydroxyphenyl)-1H-indazol-3-yl)-6,7-dihydro-1H-imidazo[4,5-c]pyridine-5(4H)-carboxamide

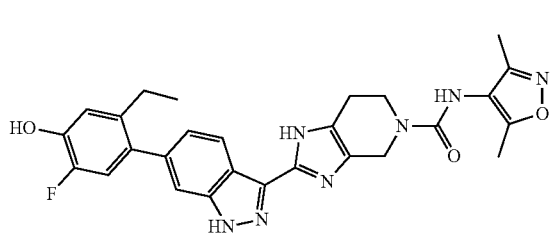 [SMILES: CCc1cc(O)c(F)cc1-c1ccc2c(-c3nc4c([nH]3)CCN(C(=O)Nc3c(C)noc3C)C4)n[nH]c2c1]

$^1$H NMR (400 MHz, DMSO-d$_6$) δ: 13.24 (s, 1H), (2×s, 12.52 and 12.44, 1H), 9.89 (s, 1H), 8.34-8.30 (m, 1H), (2×s, 8.15 and 8.05, 1H), 7.40-7.37 (s, 1H), 7.11 (dd, 1H), 7.03 (d, 1H), 6.92 (d, 1H), (3×s, 4.55, 4.45 and 4.40, 2H), (2×t, 3.80 and 3.67, 2H), 2.76-2.60 (m, 2H), 2.25 (s, 3H), 2.08 (s 3H), 1.02 (t, 3H). 2H under DMSO peak.
LCMS m/z 516 (M+H)$^+$ (ES$^+$)

(d) N-(1,3-dimethyl-2,4-dioxo-1,2,3,4-tetrahydropyrimidin-5-yl)-2-(6-(2-ethyl-5-fluoro-4-hydroxyphenyl)-1H-indazol-3-yl)-6,7-dihydro-1H-imidazo[4,5-c]pyridine-5(4H)-carboxamide

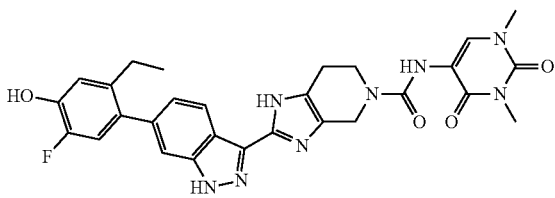 [SMILES: CCc1cc(O)c(F)cc1-c1ccc2c(-c3nc4c([nH]3)CCN(C(=O)Nc3cn(C)c(=O)n(C)c3=O)C4)n[nH]c2c1]

$^1$H NMR (400 MHz, DMSO-d$_6$) δ: 13.22 (s, 1H), 12.50-12.47 (s, 1H), 9.87 (s, 1H), 8.32 (d, 1H), 7.92 (s, 1H), (2×s, 7.83 and 7.77, 1H), 7.37 (s, 1H), 7.10 (dd, 1H), 7.02 (d, 1H), 6.92 (d, 1H), 4.54-4.51 (m, 2H), 3.81-3.71 (m, 2H), 3.32 (s, 3H), 3.21 (s, 3H), 2.75-2.66 (m, 2H), 1.02 (t, 3H). 2H under DMSO peak.

LCMS m/z 559 (M+H)+ (ES+)

(e) N-(benzo[c][1,2,5]thiadiazol-4-yl)-2-(6-(2-ethyl-5-fluoro-4-hydroxyphenyl)-1H-indazol-3-yl)-6,7-dihydro-1H-imidazo[4,5-c]pyridine-5(4H)-carboxamide

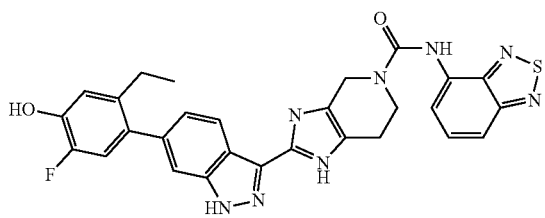 [SMILES: CCc1cc(O)c(F)cc1-c1ccc2c(-c3nc4c([nH]3)CN(C(=O)Nc3cccc5nsnc35)CC4)n[nH]c2c1]

¹H NMR (400 MHz, DMSO-d₆) δ: 13.25 (s, 1H), 12.55 (s, 1H), 9.95 (s, 1H), 9.08-8.94 (m, 1H), 8.34 (d, 1H), 7.94 (d, 1H), 7.75-7.64 (m, 2H), 7.39 (s, 1H), 7.12 (dd, 1H), 7.02 (d, 1H), 6.92 (d, 1H), 4.69 (s, 2H), 3.94-3.86 (m, 2H), 2.84-2.77 (m, 2H), 1.03 (t, 3H). 2H under DMSO peak.

LCMS m/z 555 (M+H)+ (ES+)

(f) 2-(6-(2-ethyl-5-fluoro-4-hydroxyphenyl)-1H-indazol-3-yl)-N-phenyl-6,7-dihydro-1H-imidazo[4,5-c]pyridine-5(4H)-carboxamide

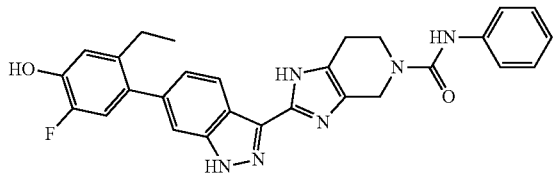 [SMILES: CCc1cc(O)c(F)cc1-c1ccc2c(-c3nc4c([nH]3)CCN(C(=O)Nc3ccccc3)C4)n[nH]c2c1]

¹H NMR (400 MHz, DMSO-d₆) δ: 13.25 (s, 1H), 12.51 (s, 1H), 9.97 (s, 1H), (2×s, 8.75 and 8.64, 1H), 8.39-8.32 (m, 1H), 7.56-7.42 (m, 2H), 7.42-7.36 (m, 1H), 7.29-7.20 (m, 2H), 7.11 (dd, 1H), 7.03 (d, 1H), 6.99-6.88 (m, 2H), 4.59 (s, 2H), 3.82 (t, 2H), 2.79-2.70 (m, 2H), 1.03 (t, 3H). 2H under DMSO peak.

LCMS m/z 497 (M+H)+ (ES+)

Example 5

5-Ethyl-2-fluoro-4-(3-(54(4-(methylsulfonyl)piperazin-1-yl)sulfonyl)-4,5,6,7-tetrahydro-1H-imidazo[4,5-c]pyridin-2-yl)-1H-indazol-6-yl)phenol

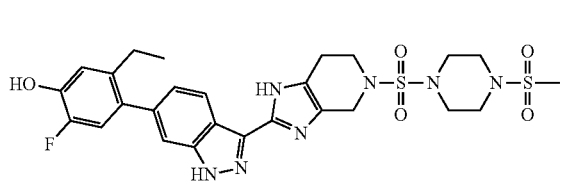 [SMILES: CCc1cc(O)c(F)cc1-c1ccc2c(-c3nc4c([nH]3)CCN(S(=O)(=O)N3CCN(S(C)(=O)=O)CC3)C4)n[nH]c2c1]

To a stirred solution of 5-ethyl-2-fluoro-4-(3-(4,5,6,7-tetrahydro-1H-imidazo[4,5-c]pyridin-2-yl)-1H-indazol-6-yl)phenol dihydrochloride (50 mg, 0.111 mmol) and DIPEA (97 µL, 0.555 mmol) in DMF (1 mL) was added 4-(methylsulfonyl)piperazine-1-sulfonyl chloride (32.1 mg, 0.122 mmol). The resulting solution was stirred at rt for 16 h. The reaction mixture was purified by preparative HPLC (Waters, Basic (0.1% Ammonium Bicarbonate), Basic, Waters X-Bridge Prep-C18, 5 µm, 19×50 mm column, 10-40% MeCN in Water) to afford the title compound (38 mg) as a white solid.

¹H NMR (400 MHz, DMSO-d₆) δ: 13.26 (s, 1H), 12.58-12.44 (m, 1H), 9.81 (s, 1H), 8.31 (d, 1H), 7.40-7.36 (m, 1H), 7.11 (dd, 1H), 7.02 (d, 1H), 6.93 (d, 1H), 4.39-4.34 (m, 2H), 3.61 (t, 2H), 3.27-3.24 (m, 4H), 3.23-3.15 (m, 4H), 2.91 (s, 3H), 2.81-2.68 (m, 2H), 1.01 (t, 3H). 2H under DMSO peak.

LCMS m/z 604 (M+H)+ (ES+)

Example 6

The following compounds were prepared by methods analogous to those described above for Example 5.

(a) N-(2-cyanoethyl)-2-(6-(2-ethyl-5-fluoro-4-hydroxyphenyl)-1H-indazol-3-yl)-N-(2-methoxyethyl)-6,7-dihydro-1H-imidazo[4,5-c]pyridine-5(4H)-sulfonamide

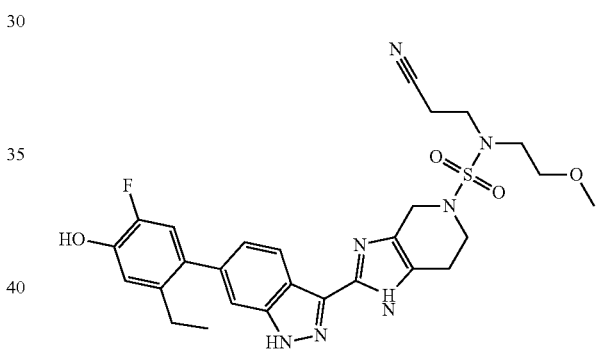

¹H NMR (400 MHz, DMSO-d₆) δ: 13.28 (s, 1H), 12.55 (s, 1H), 8.37 (s, 1H), 8.31 (d, 1H), 7.39-7.38 (m, 1H), 7.11 (dd, 1H), 7.03 (d, 1H), 6.93 (d, 1H), 4.28 (s, 2H), 3.60-3.51 (m, 6H), 3.41-3.39 (m, 2H), 3.27 (s, 3H), 2.81 (t, 2H), 2.79-2.73 (m, 2H), 1.04-0.96 (m, 3H). 2H under DMSO peak LCMS m/z 568 (M+H)+ (ES+)

(b) 1-((2-(6-(2-ethyl-5-fluoro-4-hydroxyphenyl)-1H-indazol-3-yl)-6,7-dihydro-1H-imidazo[4,5-c]pyridin-5(4H)-yl)sulfonyl)-N-methylpiperidine-4-carboxamide

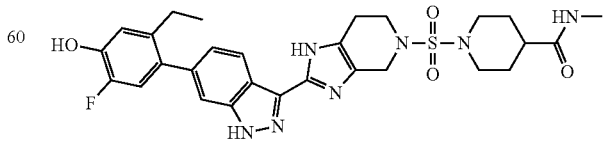

¹H NMR (400 MHz, DMSO-d₆) δ: 13.26 (s, 1H), 12.56 (s, 1H), 8.33-8.30 (m, 2H), 7.78-7.75 (m, 1H), 7.39 (s, 1H), 7.11 (dd, 1H), 7.03 (d, 1H), 6.93 (d, 1H), 4.35-4.30 (m, 2H), 3.61-3.56 (m, 4H), 2.81-2.70 (m, 4H), 2.55 (d, 3H), 2.21 (tt, 1H), 1.79-1.70 (m, 2H), 1.55 (qd, 2H), 1.02 (t, 3H). 2H under DMSO peak
LCMS m/z 582 (M+H)$^+$ (ES$^+$)

(c) 2-(6-(2-ethyl-5-fluoro-4-hydroxyphenyl)-1H-indazol-3-yl)-N-methyl-N-(tetrahydro-2H-pyran-4-yl)-6,7-dihydro-1H-imidazo[4,5-c]pyridine-5(4H)-sulfonamide

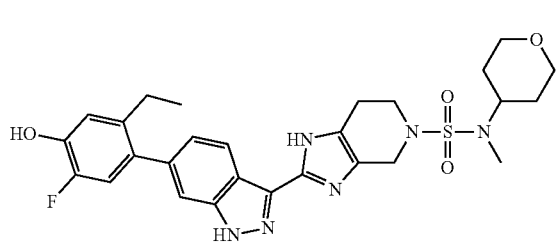 [SMILES: CCc1cc(O)c(F)cc1-c1ccc2c(-c3nc4c([nH]3)CCN(S(=O)(=O)N(C)C3CCOCC3)C4)n[nH]c2c1]

$^1$H NMR (400 MHz, DMSO-d$_6$) δ: 13.24 (s, 1H), (2×s, 12.55 and 12.43, 1H), 9.89 (s, 1H), 8.30 (d, 1H), 7.38 (s, 1H), 7.11 (dd, 1H), 7.03 (d, 1H), 6.92 (d, 1H), 4.31-4.19 (m, 2H), 3.88 (dd, 2H), 3.75, (tt, 1H), 3.56-3.47 (m, 2H), 2.78-2.67 (m, 4H), 1.77 (qd, 2H), 1.60-1.51 (m, 2H), 1.02 (t, 3H). 3H under water peak. 2H under DMSO peak.
LCMS m/z 555 (M+H)$^+$ (ES$^+$)

(d) 5-ethyl-2-fluoro-4-(3-(5-(pyrrolidin-1-ylsulfonyl)-4,5,6,7-tetrahydro-1H-imidazo[4,5-c]pyridin-2-yl)-1H-indazol-6-yl)phenol

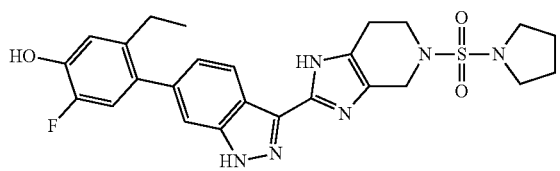 [SMILES: CCc1cc(O)c(F)cc1-c1ccc2c(-c3nc4c([nH]3)CCN(S(=O)(=O)N3CCCC3)C4)n[nH]c2c1]

$^1$H NMR (400 MHz, DMSO-d$_6$) δ: 13.26 (s, 1H), (2×s, 12.55 and 12.46, 1H), 9.90 (s, 1H), 8.31 (dd, 1H), 7.38 (s, 1H), 7.11 (dd, 1H), 7.02 (d, 1H), 6.92 (d, 1H), 4.31 (2×s, 4.35 and 4.29, 2H), 3.57 (t, 2H), 3.24 (t, 4H), 2.78-2.71 (m, 2H), 1.88-1.82 (m, 4H), 1.02 (t, 3H). 2H under DMSO peak.
LCMS m/z 511 (M+H)$^+$ (ES$^+$)

(e) 5-ethyl-2-fluoro-4-(3-(5-(morpholinosulfonyl)-4,5,6,7-tetrahydro-1H-imidazo[4,5-c]pyridin-2-yl)-1H-indazol-6-yl)phenol

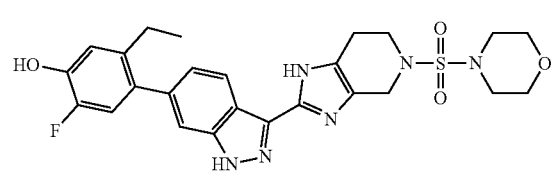 [SMILES: CCc1cc(O)c(F)cc1-c1ccc2c(-c3nc4c([nH]3)CCN(S(=O)(=O)N3CCOCC3)C4)n[nH]c2c1]

1H NMR (400 MHz, DMSO-d$_6$) δ: 13.26 (s, 1H), (2×s, 12.57 and 12.47, 1H), 9.92 (s, 1H), 8.30 (dd, 1H), 7.38 (s, 1H), 7.11 (dd, 1H), 7.02 (d, 1H), 6.91 (d, 1H), 4.44-4.31 (m, 2H), 3.68-3.56 (m, 6H), 3.17-3.08 (m, 4H), 2.79-2.70 (m, 2H), 1.02 (t, 3H). 2H under DMSO peak.
LCMS m/z 527 (M+H)$^+$ (ES$^+$)

(f) 5-ethyl-2-fluoro-4-(3-(5-((4-methylpiperazin-1-yl)sulfonyl)-4,5,6,7-tetrahydro-1H-imidazo[4,5-c]pyridin-2-yl)-1H-indazol-6-yl)phenol

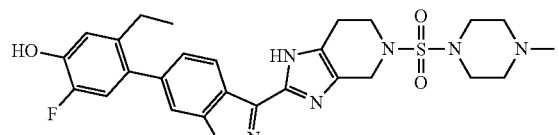

$^1$H NMR (400 MHz, DMSO-d$_6$) δ: 13.25 (s, 1H), (2×s, 12.57 and 12.46, 1H), 9.87 (s, 1H), 8.33-8.30 (m, 1H), 7.40-7.36 (m, 1H), 7.12 (dd, 1H), 7.03 (d, 1H), 6.92 (d, 1H), 4.38-4.32 (m, 2H), 3.59 (t, 2H), 3.18-3.13 (m, 4H), 2.75-2.73 (m, 2H), 2.37-2.34 (m, 4H), 2.18 (s, 3H), 1.02 (t, 3H). 2H under DMSO peak.
LCMS m/z 540 (M+H)$^+$ (ES$^+$)

(g) 4-((2-(6-(2-ethyl-5-fluoro-4-hydroxyphenyl)-1H-indazol-3-yl)-6,7-dihydro-1H-imidazo[4,5-c]pyridin-5(4H)-yl)sulfonyl)thiomorpholine 1,1-dioxide

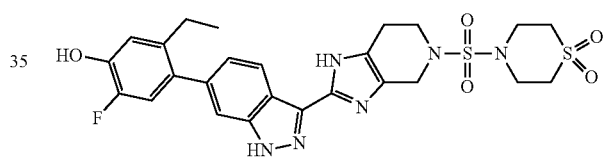

$^1$H NMR (400 MHz, DMSO-d$_6$) δ: 13.26 (s, 1H), (2×s, 12.59 and 12.49, 1H), 9.98 (s, 1H), 8.31 (d, 1H), 7.39 (s, 1H), 7.11 (dd, 1H), 7.03 (d, 1H), 6.92 (d, 1H), 4.43-4.26 (m, 2H), 3.74-3.65 (m, 4H), 3.62 (t, 2H), 3.29-3.18 (m, 4H), 2.82-2.72 (m, 2H), 1.02 (t, 3H). 2H under DMSO peak.

(h) 4-((2-(6-(2-ethyl-5-fluoro-4-hydroxyphenyl)-1H-indazol-3-yl)-6,7-dihydro-1H-imidazo[4,5-c]pyridin-5(4H)-yl)sulfonyl)piperazine-1-carbaldehyde

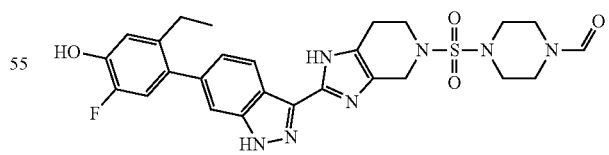

$^1$H NMR (400 MHz, DMSO-d$_6$) δ: 13.24 (s, 1H), (2×s, 12.55 and 12.45, 1H), 9.88 (s, 1H), 8.30 (d, 1H), 8.03 (s, 1H), 7.38 (s, 1H), 7.10 (dd, 1H), 7.01 (d, 1H), 6.91 (d, 1H), 4.43-4.30 (m, 2H), 3.60 (t, 2H), 3.47-3.43 (m, 4H), 3.20 (t, 2H), 3.14 (t, 2H), 2.81-2.70 (m, 2H), 1.02 (t, 3H). 2H under DMSO peak.
LCMS m/z 554 (M+H)$^+$ (ES$^+$)

(i) 5-Ethyl-2-fluoro-4-(3-(5-((4-methoxypiperidin-1-yl)sulfonyl)-4,5,6,7-tetrahydro-1H-imidazo[4,5-c]pyridin-2-yl)-1H-indazol-6-yl)phenol

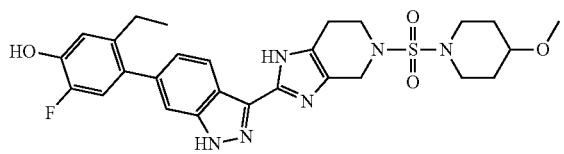 [SMILES: CCc1cc(O)c(F)cc1-c1ccc2c(-c3nc4c([nH]3)CCN(S(=O)(=O)N3CCC(OC)CC3)C4)n[nH]c2c1]

$^1$H NMR (400 MHz, DMSO-$d_6$) δ: 13.25 (s, 1H), 12.58 (s, 1H), 9.85 (s, 1H), 8.31 (dd, 1H), 7.38 (s, 1H), 7.11 (dd, 1H), 7.02 (d, 1H), 6.91 (d, 1H), 4.31 (s, 2H), 3.56 (t, 2H), 3.23 (s, 3H), 3.00 (tt, 2H), 2.75-2.70 (m, 2H), 1.88-1.83 (m, 2H), 1.53-1.45 (m, 2H), 1.02 (t, 3H). 3H under water peak. 2H under DMSO peak.

Biological Testing: Experimental Methods

Enzyme Binding Assays (Kinomescan)

Kinase enzyme binding activities of compounds disclosed herein may be determined using a proprietary assay which measures active site-directed competition binding to an immobilized ligand (Fabian, M. A., et al., *Nature Biotechnol.* 2005, 23, 329-336). These assays may be conducted by DiscoveRx (formerly Ambit; San Diego, Calif.). The percentage inhibition produced by incubation with a test compound may be calculated relative to the non-inhibited control.

Cellular Assays

The compounds of the invention were studied using one or more of the following assays.

(a) IFNγ Release from CD3/IL2 Stimulated PBMC Cells

PBMCs from healthy subjects are separated from whole blood using a density gradient (Lymphoprep, Axis-Shield Healthcare). Cells are added to a 96 well plate, and compound at the desired concentration added 2 hours prior to stimulation with a mixture of monoclonal antibody to CD3 (1 μg/ml, eBioscience) and human recombinant IL2 (10 ng/ml, Peprotech). After 48 hours incubation under normal tissue culture conditions, supernatants are collected and IFNγ release determined by Sandwich ELISA (Duo-set, R&D System). The $IC_{50}$ is determined from the dose response curve.

(b) IL-2 and IFNγ Release in CD3/CD28 Stimulated LPMC Cells from IBD Patients

Lamina propria mononuclear cells (LPMCs) are isolated and purified from inflamed IBD mucosa of surgical specimens or from normal mucosa of surgical specimens as follows: The mucosa is removed from the deeper layers of the surgical specimens with a scalpel and cut in fragments of size 3-4 mm. The epithelium is removed by washing the tissue fragments three times with 1 mM EDTA (Sigma-Aldrich, Poole, UK) in HBSS (Sigma-Aldrich) with agitation using a magnetic stirrer, discarding the supernatant after each wash. The sample is subsequently treated with type 1A collagenase (1 mg/mL; Sigma-Aldrich) for 1 h with stirring at 37° C. The resulting cell suspension is then filtered using a 100 μm cell strainer, washed twice, resuspended in RPMI-1640 medium (Sigma-Aldrich) containing 10% fetal calf serum, 100 U/mL penicillin and 100 μg/mL streptomycin, and used for cell culture.

Freshly isolated LPMCs ($2 \times 10^5$ cells/well) are stimulated with 1 μg/mL α-CD3/α-CD28 for 48 h in the presence of either DMSO control or appropriate concentrations of compound. After 48 h, the supernatant is removed and assayed for the presence of TNFα and IFNγ by R&D ELISA. Percentage inhibition of cytokine release by the test compounds is calculated relative to the cytokine release determined for the DMSO control (100%).

(c) Cell Cytotoxicity Assay $1 \times 10^5$ Jurkat cells (immortalised human T lymphocytes) are added to the appropriate number of wells of a 96 well plate in 100 μL of media (RPMI supplemented with 10% foetal bovine serum). 1 μL of DMSO control (final concentration 1.0% v/v) or test compound (final concentration 20, 5 or 1 μg/mL) is added to the wells and incubated at 37° C., 5% $CO_2$. After 24 hours, the plate is centrifuged at 1200 rpm for 3 minutes and the supernatant discarded. Cells are then resuspended in 150 μL (final concentration 7.5 μg/mL) of propidium iodide (PI) in PBS and incubated at 37° C., 5% $CO_2$ for 15 minutes. After 15 minutes, cells are analysed by flow cytometry (BD accuri) using the FL3 window. The % viability is calculated as the % of cells that are PI negative in the test wells normalised to the DMSO control.

In Vivo Screening: Pharmacodynamics and Anti-inflammatory Activity (i) DSS-Induced Colitis in Mice Non-fasted, 10-12 week old, male BDF1 mice are dosed by oral gavage twice daily with either vehicle, reference item (5-ASA) or test compound one day before (Day −1) stimulation of the inflammatory response by treatment with dextran sodium sulphate (DSS). On Day 0 of the study, DSS (5% w/v) is administered in the drinking water followed by BID dosing of the vehicle (5 mL/kg), reference (100 mg/kg) or test compound (5 mg/kg) for 7 days. The drinking water with DSS is replenished every 3 days. During the study, animals are weighed every day and stool observations are made and recorded as a score, based on stool consistency. At the time of sacrifice on Day +6, the large intestine is removed and the length and weight are recorded. Sections of the colon are taken for either MPO analysis, to determine neutrophil infiltration, or for histopathology scoring to determine disease severity.

(ii) TNBS-Induced Colitis in Mice

Non-fasted, 10-12 week old, male BDF1 mice are dosed by oral gavage twice daily with either vehicle (5 mL/kg), reference item (Budesonide 2.5 mg/kg) or test compound (1 or 5 mg/kg) one day before (Day −1) stimulation of the inflammatory response by treatment with 2,4,6-trinitrobenzenesulphonic acid (TNBS) (15 mg/mL in 50% ethanol/50% saline). On Day 0 of the study TNBS (200 μL) is administered intra-colonically via a plastic catheter with BID dosing of the vehicle, reference or test compound continuing for 2 or 4 days. During the study, animals are weighed every day and stool observations are made and recorded as a score, based on stool consistency. At the time of sacrifice on Day 2 (or Day 4), the large intestine is removed and the length and weight recorded. Sections of the colon are taken for histopathology scoring to determine disease severity.

(iii) Adoptive Transfer in Mice

On Study day 0, female Balb/C mice are terminated and spleens obtained for CD45RB$^{high}$ cell isolation (Using SCID IBD cell Separation protocol). Approximately $4 \times 10^5$ cells/mL CD45RB$^{high}$ cells are then injected intraperitoneally (100 μL/mouse) into female SCID animals. On study day 14, mice are weighed and randomized into treatment groups based on body weight. On Day 14, compounds are administered BID, via oral gavage, in a dose volume of 5 mL/kg. Treatment continues until study day 49, at which point the animals are necropsied 4 hours after the morning administration. The colon length and weight are recorded and used as a secondary endpoint in the study as a measurement of colon oedema. The colon is then divided into six cross-sections, four of which are used for histopathology scoring (primary endpoint) and two are homogenised for cytokine analysis. Data is given as the % inhibition of the induction window between naïve animals and vehicle animals, where higher inhibition implies closer to the non-diseased, naïve, phenotype.

(iv) Endotoxin-Induced Uveitis in Rats

Male, Lewis rats (6-8 weeks old, Charles River UK Limited) are housed in cages of 3 at 19-21° C. with a 12 h light/dark cycle (07:00/19:00) and fed a standard diet of rodent chow and water ad libitum. Non-fasted rats are weighed, individually identified on the tail with a permanent marker, and receive a single intravitreal administration into the right vitreous humor (5 μL dose volume) of 100 ng/animal of LPS (Escherichia coli 0111:64 prepared in PBS, Sigma Aldrich, UK) using a 32-gauge needle. Untreated rats are injected with PBS. Test compound or vehicle (4% polyoxyl 40 stearate, 4% mannitol in PBS (pH 7.4)) are administered by the topical route onto the right eye (10 μL) of animals 1 hour prior to LPS, at the time of LPS administration, and 1, 2 and 4 hours post LPS administration. Before administration, the solution to be administered is sonicated to ensure a clear solution. 6 hours after LPS dosing, animals are euthanized by overdose with pentobarbitone (via cardiac puncture). Immediately after euthanasia, 10 μL of aqueous humor is collected from the right eye of the rats by puncture of the anterior chamber using a 32 gauge needle under a surgical microscope. The aqueous humor is diluted in 20 μL of PBS and total cell counts are measured immediately using a Countess automated cell counter (Invitrogen). Following collection of the aqueous humour, the right eye of each animal is enucleated and dissected into front (anterior) and back (posterior) sections around the lens. Each section is weighed and homogenised in 500 μL of sterile PBS followed by 20 minutes centrifugation at 12000 rpm at 4° C. The resulting supernatant is divided into 3 aliquots and stored at −80° C. until subsequent cytokine analysis by R&D DuoSet ELISA.

Summary of In Vitro and In Vivo Screening Results

The compound of Example 2(k) is substantially more potent than the Reference Compound, displaying lower dissociation constants in the biochemical JAK family enzyme binding assays carried out at DiscoveRx (Table 1).

TABLE 1

Dissociation constants for selected kinases determined by LeadHunter Discover Services (DiscoveRx Corporation, Fremont, CA), using the KINOMEscan ™ technology.

| Test compound | Dissociation Constant (nM) | | | |
| --- | --- | --- | --- | --- |
|  | JAK1 | JAK2 | JAK3 | TYK2 |
| Reference Compound | 2.7 | 0.78 | 1.9 | 1.9 |
| Example 1 | 0.62 | 0.052 | 0.098 | 0.11 |
| Example 2(a) | 0.60 | 0.034 | 0.046 | 0.069 |

Similarly, compounds of the examples of the present invention may be substantially more potent than the Reference Compound on inhibiting IFNγ release from CD3/IL2-stimulated PBMC cells (assay (a) above) and/or may display enhanced viabilities in cell cytotoxicity assay (c) above (Table 2).

TABLE 2

Effects of the compounds of the invention on inhibition of IFN$_\gamma$ release from stimulated PBMC cells (assay (a) above) and cell viability in Jurkat cells (assay (c) above).

| Test compound | PBMC IFN$_\gamma$ IC$_{50}$ (nM) | % viability at 1 μg/mL |
| --- | --- | --- |
| Reference Compound | 81.3 | 49 |
| Example 1 | 3.6 | 40 |
| Example 2(a) | 48.4 | 59 |
| Example 2(b) | 31.3 | — |
| Example 2(c) | 129.2 | 99 |
| Example 2(d) | 5.1 | — |
| Example 2(e) | 10.9 | 92 |
| Example 3 | 19.5 | 91 |
| Example 4(a) | 14.6 | 60 |
| Example 4(b) | 54.8 | — |
| Example 4(c) | 44.2 | — |
| Example 4(d) | 19.2 | 60 |
| Example 4(e) | 30.9 | — |
| Example 4(f) | 19.6 | — |
| Example 5 | 17.8 | 87 |
| Example 6(a) | 9.5 | 79 |
| Example 6(b) | 100.5 | — |
| Example 6(c) | 9.3 | 76 |
| Example 6(d) | 8.3 | 74 |
| Example 6(e) | 4.7 | 64 |
| Example 6(f) | 9.0 | 29 |
| Example 6(g) | 7.2 | 88 |
| Example 6(h) | 37.4 | 93 |
| Example 6(i) | 14.0 | 86 |

Summary of Additional Studies

Determination of Solubilities in Fasted-State Simulated Colonic Fluid (FaSSCoF)

The solubilities of compounds of the invention in FaSSCoF at pH 6.5 are determined using a modification of a previously-reported procedure (Vertzoni, M., et al. *Pharm. Res.* 2010, 27, 2187-2196). In place of the bile salt extract employed in the original procedure (which extract is no longer available), the modified procedure uses a mixture of sodium taurochlorate (0.15 g), glycocholic acid (0.15 g), ursodeoxycholic acid (0.05 g), cholic acid (0.05 g), and glycodeoxycholic acid (0.05 g). These five bile acids are ground together with a mortar and pestle to produce a fine white powder that is incorporated into the FaSSCoF, as outlined below.

FaSSCoF medium: Tris(hydroxymethyl)aminomethane (Tris; 0.275 g) and maleic acid (0.44 g) are dissolved in water (35 mL) to give a solution whose pH is adjusted to 6.5 by treatment with 0.5M NaOH (ca. 12 mL). The solution is then made up to 50 mL with water. A portion of this Tris/maleate buffer solution (ca. 25 mL) is added to a 0.5 L round-bottomed flask, before being treated with 0.00565 g of the bile acid mixture described above. Solutions of phosphatidylcholine (0.0111 g) in DCM (0.15 mL) and palmitic acid (0.0013 g) in DCM (0.15 mL) are added, then the organic solvent is evaporated off under reduced pressure at 40° C. until a clear solution, with no perceptible DCM odour, is achieved. The volume of the evaporated solution is adjusted to 50 mL by addition of the remainder of Tris/maleate buffer, then BSA (0.115 g) is added, before being dissolved by gentle agitation.

Solubility Determination: Test compounds are suspended in the pH 6.5 FaSSCoF medium to give a maximum final concentration of 2-10 mg/mL. The suspensions are equilibrated at 25° C. for 24 h, before being filtered through a glass fibre C filter. The filtrates are then diluted as appropriate for injection and quantification by HPLC with reference to a standard. Different volumes of the standard, diluted and undiluted sample solutions are injected and the solubilities are calculated using the peak areas determined by integration of the peak found at the same retention time as the principal peak in the standard injection.

FaSSCoF solubilities are shown in Table 3 below, which reveals that, unlike the Reference Compound, compounds of the Examples exhibited solubilities in the FaSSCoF medium at pH 6.5 of 0.01 mg/mL or greater.

plasma exposure was very low. The very low plasma exposure observed for Example 1 was substantially less than that found for the Reference Compound. Conversely, colonic exposure was markedly greater for Example 1 ($AUC_{0-24\,h}$= 132,979 h·ng/g) compared to the Reference Compound ($AUC_{0-24\,h}$=43,739 h·ng/g). In Table 4, "P" refers to plasma and "C" refers to total colon.

TABLE 4

Mean plasma concentrations (ng/mL) or total colon levels (ng/g) obtained following oral administration of the Reference Compound and Example 1 to mice at 10 mg/kg in solution in 20% aqueous hydroxypropyl-β-cyclodextrin (dose volume = 10 mL/kg).

| Com- | | Time (h) | | | | | | | |
|---|---|---|---|---|---|---|---|---|---|
| pound | Matrix | 0.5 | 1 | 2 | 4 | 6 | 8 | 12 | 24 |
| Reference Compound | P | 5.2 | 12.8 | 2.2 | 14.4 | 114 | 95.0 | 0.0 | 0.0 |
|  | C | 344 | 102 | 2,366 | 2,972 | 201 | 2,555 | 3,229 | 16.6 |
| Example 1 | P | 6.1 | 1.8 | 1.9 | 0.0 | 0.0 | 0.0 | 0.0 | 0.0 |
|  | C | 327 | 984 | 19,722 | 4,686 | 8,438 | 11,942 | 4,791 | 350 |

TABLE 3

Solubilities measured for certain compounds of the Examples of the present invention in FaSSCoF at pH 6.5.

| | pH 6.5 FaSSCoF Solubility (mg/mL) | |
|---|---|---|
| Test compound | Run 1 | Run 2 |
| Reference Compound | 0.006 | 0.006 |
| Example 1 | 0.040 | 0.020 |
| Example 2(a) | 0.030 | 0.030 |

Determination of Pharmacokinetic Parameters

Studies were conducted by Sai Life Sciences (Hinjewadi, Pune, India) to investigate the systemic pharmacokinetics and total colon tissue distribution of compounds of the invention following a single oral administration in male C57BL/6 mice.

A group of twenty four male mice were administered with a solution of test compound formulated at a dose of 10 mg/10 mL/kg in aqueous hydroxypropyl-β-cyclodextrin (20% w/v in water). Blood samples (approximately 60⁴) were collected from retro-orbital plexus of each mouse under light isoflurane anaesthesia such that the samples were obtained at 0.5, 1, 2, 4, 6, 8, 12 and 24 hr. The blood samples were collected from a set of three mice at each time point in a labeled micro centrifuge tube containing $K_2EDTA$ as anticoagulant. Plasma samples were separated by centrifugation at 4000 rpm for 10 min and stored below −70° C. until bioanalysis. After collection of blood sample, animals were humanely euthanized by carbon dioxide asphyxiation to collect total colon tissues. The colons were flushed with cold PBS (pH7.4) to remove contents. The total colon tissues were homogenized with cold PBS (pH7.4) of twice the weight of colon tissue and stored below −70° C. Total volume was three times the total colon tissue weights. All samples were processed for analysis by protein precipitation using acetonitrile and analyzed with a fit-for-purpose LC-MS/MS method. Pharmacokinetic parameters were calculated using the non-compartmental analysis tool of Phoenix WinNonlin® (Version 6.3).

The data catalogued in Table 4 reveal that, following oral administration, the compound of Example 1 achieved substantial colonic concentrations, while, in contrast, systemic Abbreviations
aq aqueous
5-ASA 5-aminosalicylic acid
ATP adenosine-5'-triphosphate
BID bis in die (twice-daily)
Boc tert-butoxycarbonyl
br broad
BSA bovine serum albumin
CD Crohn's disease
COPD chronic obstructive pulmonary disease
d doublet
δ chemical shift
DCM dichloromethane
DIPEA diisopropylethylamine
DMEM Dulbecco's modified eagle medium
DMF N,N-dimethylformamide
DMSO dimethyl sulfoxide
EDTA ethylenediaminetetraacetic acid
ELISA enzyme-linked immunosorbent assay
(ES⁻) electrospray ionization, negative mode
(ES⁺) electrospray ionization, positive mode
Et ethyl
$Et_3N$ triethylamine
EtOAc ethyl acetate
EtOH ethanol
FaSSCoF fasted-state simulated colonic fluid
FBS foetal bovine serum
FCS foetal calf serum
HATU 2-(1H-7-azabenzotriazol-1-yl)-1,1,3,3-tetramethyl uronium hexafluoro-phosphate
HBSS Hank's balanced salt solution
HPLC high performance liquid chromatography
HPMC hydroxypropylmethylcellulose
h, hr or hrs hour(s)
HRP horseradish peroxidise
IBD Inflammatory bowel disease
IFNγ interferon-γ
IL interleukin
IPA isopropyl alcohol
JAK Janus kinase
JNK c-Jun N-terminal kinase
LC liquid chromatography
LPMC lamina propria mononuclear cells LPS lipopolysaccharide
m multiplet
(M+H)+ protonated molecular ion
(M−H)− deprotonated molecular ion
Me methyl
MeCN acetonitrile
MeOH methanol
MHz megahertz
min or mins minute(s)
MMAD mass median aerodynamic diameter
MPO myeloperoxidase
MS mass spectrometry
m/z mass-to-charge ratio
NMP N-Methyl-2-pyrrolidone
NMR nuclear magnetic resonance (spectroscopy)
OD optical density
PBMC peripheral blood mononuclear cell
PBS phosphate buffered saline
Ph phenyl
PHA phytohaemagglutinin
PI propidium iodide
PMA phorbol myristate acetate
q quartet
rt or RT room temperature
RP HPLC reverse phase high performance liquid chromatography
rpm revolutions per minute
RPMI Roswell Park Memorial Institute
s singlet
sat or satd saturated
SCID severe combined immunodeficiency
SCX solid supported cation exchange (resin)
SDS sodium dodecyl sulfate
$S_NAr$ nucleophilic aromatic substitution
Syk Spleen tyrosine kinase
t triplet
$^t$Bu tert-butyl
T3P 1-propanephosphonic acid cyclic anhydride
TEA triethylamine
THF tetrahydrofuran
TFA trifluoroacetic acid
TGFβ transforming growth factor beta
TNFα tumor necrosis factor alpha
Tris tris(hydroxymethyl)aminomethane
TYK2 tyrosine kinase 2
UC ulcerative colitis
UPLC ultra performance liquid chromatography
UV ultra-violet Prefixes n-, s-, i-, t- and tert- have their usual meanings: normal, secondary, iso, and tertiary.

The invention claimed is:

1. A pharmaceutical formulation comprising a pharmaceutically acceptable adjuvant, diluent or carrier and a compound having the structure of Formula Ia,

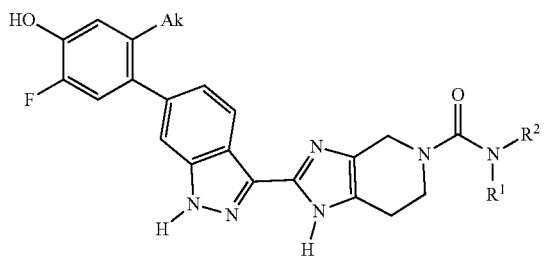

Ia or pharmaceutically acceptable salt, solvate or isotopic derivative thereof, wherein:

X represents halo;

Ak represents $C_{1-6}$ alkyl optionally substituted by one or more fluorine atoms;

$R^1$ and $R^2$ each independently represents H, $C_{1-6}$ alkyl, $C_{3-7}$ cycloalkyl, aryl, heteroaryl, or heterocyclyl, which latter five groups are optionally substituted by one or more substituents selected from halo, cyano, —C(O)OH, oxo, —$NR^3SO_2R^4$, —N=S(O)($R^4$)$_2$, —S(O)$_m$$R^5$, —P(O)($R^4$)$_2$, —C(O)$NR^5R^6$, —S(O)$_2$$NR^5R^6$, —(OCH$_2$CH$_2$)$_{0-4}$$OR^5$, —(CH$_2$)$_{0-4}$—$NR^5R^6$, $C_{1-6}$ alkyl, $C_{2-6}$ alkenyl, $C_{2-6}$ alkynyl, $C_{3-7}$ cycloalkyl, aryl, heteroaryl or heterocyclyl, which latter seven groups are optionally substituted by one or more substituents selected from halo, cyano, —C(O)OH, $C_{1-4}$ alkyl, $C_{1-4}$ alkoxy, oxo and hydroxy;

or $R^1$ and $R^2$, together with the N-atom to which they are attached, form a 4- to 7-membered heterocyclic group that is fully saturated or partially unsaturated and which heterocyclic group contains one N atom (the atom to which $R^1$ and $R^2$ are attached) and, optionally, one or more further heteroatoms selected from O, S and N, and which heterocyclic group is optionally fused to a benzene or heteroaromatic ring, and which heterocyclic group is optionally substituted by one or more substituents selected from halo, hydroxy, oxo, —C(O)OH, —$NR^3SO_2R^4$, —S(O)$_m$$R^5$, —C(O)$NR^5R^6$, —(CH$_2$)$_{0-4}$—$NR^5R^6$, —(OCH$_2$CH$_2$)$_{0-4}$$OR^5$, $C_{1-4}$ alkyl, $C_{1-4}$ alkoxy, aryl, heteroaryl, and heterocyclyl, which latter five groups are optionally substituted by one or more substituents selected from halo, cyano, —C(O)OH, $C_{1-4}$ alkyl, $C_{1-4}$ alkoxy, oxo and hydroxy;

$R^3$ represents H or $C_{1-4}$ alkyl optionally substituted by one or more substituents selected from halo, hydroxy and $C_{1-2}$ alkoxy;

$R^4$ represents $C_{1-4}$ alkyl, $C_{3-7}$ cycloalkyl, aryl, heteroaryl or heterocyclyl, which latter five groups are optionally substituted by one or more substituents selected from halo, cyano, —C(O)OH, $C_{1-4}$ alkyl, oxo, hydroxy and $C_{1-4}$ alkoxy;

$R^5$ and $R^6$ each independently represent H, $C_{1-6}$ alkyl, $C_{3-7}$ cycloalkyl, aryl, heteroaryl, or heterocyclyl, which latter five groups are optionally substituted by one or more substituents selected from halo, cyano, —C(O)OH, oxo, hydroxy, $C_{1-4}$ alkyl, $C_{1-4}$ alkoxy, —S(O)$_p$$R^7$, —C(O)$NR^aR^b$ and —(CH$_2$)$_{0-4}$—$NR^aR^b$, or [C($R^{6b}$)($R^{6c}$)CH$_2$Z]$_{1-12}$—CH$_2$CH$_2$—$R^{6a}$ or —C($R^{6b}$)($R^{6c}$)—[$C_{1-5}$ alkylene]-$R^{6a}$;

or $R^5$ and $R^6$, together with the N-atom to which they are attached, form a 4- to 7-membered heterocyclic group that is fully saturated or partially unsaturated and which heterocyclic group contains one N atom (the atom to which $R^5$ and $R^6$ are attached) and, optionally, one or more further heteroatoms selected from O, S and N, and which heterocyclic group is optionally substituted by one or more substituents selected from halo, hydroxy, oxo, —C(O)OH, —S(O)$_p$$R^7$, —C(O)$NR^aR^b$, —(CH$_2$)$_{0-4}$—$NR^aR^b$, —(OCH$_2$CH$_2$)$_{0-4}$$OR^c$, $C_{1-4}$ alkyl, $C_{1-4}$ alkoxy, aryl, heteroaryl and heterocyclyl, which latter five groups are optionally substituted by one or more substituents selected from halo, cyano, —C(O)OH, $C_{1-4}$ alkyl, $C_{1-4}$ alkoxy, oxo and hydroxy;

Z represents, independently upon each occurrence, —O—, —C(O)N($R^8$)— or —N($R^8$)C(O)—;

$R^{6a}$ represents —$OR^{7a}$, —S(O)$_p$$R^7$, —N($R^{7b}$)$R^{7c}$ or —C(O)OH;

$R^{6b}$, $R^{6c}$ and $R^8$ independently represent H or methyl;

$R^a$, $R^b$ and $R^c$ independently represent H or $C_{1-4}$ alkyl optionally substituted by one or more substituents selected from halo, hydroxy and —C(O)OH, or $R^a$ and $R^b$, together with the N-atom to which they are attached, form a 4- to 7-membered heterocyclic group that is fully saturated, partially unsaturated or fully aromatic and which heterocyclic group contains one N atom (the atom to which $R^a$ and $R^b$ are attached) and, optionally, one or more further heteroatoms selected from O, S and N, and which heterocyclic group is optionally substituted by one or more substituents selected from halo, hydroxy, oxo, —C(O)OH, $C_{1-4}$ alkyl, $C_{1-4}$ alkoxy and $C_{1-4}$ hydroxyalkyl;

$R^7$ represents $C_{1-4}$ alkyl optionally substituted by one or more substituents selected from halo, hydroxy and $C_{1-4}$ alkoxy;

$R^{7a}$ to $R^{7c}$ independently represent H or $C_{1-4}$ alkyl optionally substituted by one or more halo atoms or by —C(O)OH, or $R^{7b}$ and/or $R^{7c}$ represents —[$C_a$ alkylene]-[$C_b$ alkylene]-$OR^{7d}$, or $R^{7b}$ and $R^{7c}$ together with the N-atom to which they are attached, form a 4- to 7-membered heterocyclic group that is fully saturated, partially unsaturated or fully aromatic and which heterocyclic group contains one N atom (the atom to which $R^{7b}$ and $R^{7c}$ are attached) and, optionally, one or more further heteroatoms selected from O, S and N, and which heterocyclic group is optionally substituted by one or more substituents selected from halo, hydroxy, oxo, —C(O)OH, $C_{1-4}$ alkyl, $C_{1-4}$ alkoxy and $C_{1-4}$ hydroxyalkyl;

a and b independently represent an integer selected from 1, 2 and 3, wherein the sum of a and b is 2, 3 or 4;

$R^{7d}$ represents H or $C_{1-4}$ alkyl optionally substituted by one or more halo atoms: and m and p represent, independently upon each occurrence, 0, 1 or 2.

2. The pharmaceutical composition of claim 1, wherein X represents fluoro and/or Ak represents $C_{1-3}$ alkyl.

3. The pharmaceutical composition of claim 1, wherein:
$R^1$ and $R^2$ independently represent H, heterocyclyl, $C_{1-2}$ alkyl or phenyl, which latter two groups are optionally substituted by one or more substituents selected from heterocyclyl, halo, cyano, —$OR^{5a}$ and methyl, which latter group is optionally substituted by one or more halo atoms; and $R^{5a}$ represents H or $C_{1-2}$ alkyl.

4. The pharmaceutical composition of claim 1, wherein:
$R^1$ and $R^2$, together with the N-atom to which they are attached, form a 5- or 6-membered heterocyclic group that is fully saturated and which heterocyclic group contains one N atom (the atom to which $R^1$ and $R^2$ are attached) and, optionally, one or two further heteroatoms selected from O, S and N, and which heterocyclic group is optionally fused to a benzene ring, and which heterocyclic group is optionally substituted by one or more substituents selected from halo, oxo, —$S(O)_2R^{5b}$, $C_{1-3}$ alkyl, $C_{1-3}$ alkoxy and heterocyclyl; and $R^{5b}$ represents $C_{1-2}$ alkyl.

5. The pharmaceutical composition of claim 1, wherein each heterocyclyl group independently represents a 5- or 6-membered heterocyclic ring that is fully saturated, which group contains one or two heteroatoms selected from N, O and S.

6. The pharmaceutical composition of claim 1, wherein the compound is:

[1,4'-bipiperidin]-1'-yl(2-(6-(2-ethyl-5-fluoro-4-hydroxyphenyl)-1H-indazol-3-yl)-1,4,6,7-tetrahydro-5H-imidazo[4,5-c]pyridin-5-yl)methanone;

(2-(6-(2-ethyl-5-fluoro-4-hydroxyphenyl)-1H-indazol-3-yl)-1,4,6,7-tetrahydro-5H-imidazo[4,5-c]pyridin-5-yl)(indolin-1-yl)methanone;

1-ethyl-4-(2-(6-(2-ethyl-5-fluoro-4-hydroxyphenyl)-1H-indazol-3-yl)-4,5,6,7-tetrahydro-1H-imidazo[4,5-c]pyridine-5-carbonyl)piperazine-2,3-dione;

2-(6-(2-ethyl-5-fluoro-4-hydroxyphenyl)-1H-indazol-3-yl)-N-((tetrahydro-2H-pyran-4-yl)methyl)-6,7-dihydro-1H-imidazo[4,5-c]pyridine-5 (4H)-carboxamide;

2-(6-(2-ethyl-5-fluoro-4-hydroxyphenyl)-1H-indazol-3-yl)-N-(2-(2-methoxyethoxy)ethyl)-6,7-dihydro-1H-imidazo[4,5-c]pyridine-5 (4H)-carboxamide;

2-(6-(2-ethyl-5-fluoro-4-hydroxyphenyl)-1H-indazol-3-yl)-N-(4-(methylsulfonyl)phenyl)-6,7-dihydro-1H-imidazo[4,5-c]pyridine-5 (4H)-carboxamide;

N-(3,5-dimethylisoxazol-4-yl)-2-(6-(2-ethyl-5-fluoro-4-hydroxyphenyl)-1H-indazol-3-yl)-6,7-dihydro-1H-imidazo[4,5-c]pyridine-5 (4H)-carboxamide;

N-(1,3-dimethyl-2,4-dioxo-1,2,3,4-tetrahydropyrimidin-5-yl)-2-(6-(2-ethyl-5-fluoro-4-hydroxyphenyl)-1H-indazol-3-yl)-6,7-dihydro-1H-imidazo[4,5-c]pyridine-5 (4H)-carboxamide;

N-(benzo[c][1,2,5]thiadiazol-4-yl)-2-(6-(2-ethyl-5-fluoro-4-hydroxyphenyl)-1H-indazol-3-yl)-6,7-dihydro-1H-imidazo[4,5-c]pyridine-5(4H)-carboxamide; or 2-(6-(2-ethyl-5-fluoro-4-hydroxyphenyl)-1H-indazol-3-yl)-N-phenyl-6,7-dihydro-1H-imidazo[4,5-c]pyridine-5(4H)-carboxamide;

or a pharmaceutically acceptable salt, solvate or isotopic derivative thereof.

7. The pharmaceutical composition of claim 1, wherein the compound is (2-(6-(2-ethyl-5-fluoro-4-hydroxyphenyl)-1H-indazol-3-yl)-1,4,6,7-tetrahydro-5H-imidazo[4,5-c]pyridin-5-yl)(morpholino)methanone, or a pharmaceutically acceptable salt, solvate or isotopic derivative thereof.

8. The pharmaceutical composition of claim 1, wherein the compound is (2-(6-(2-ethyl-5-fluoro-4-hydroxyphenyl)-1H-indazol-3-yl)-1,4,6,7-tetrahydro-5H-imidazo[4,5-c]pyridin-5-yl)(pyrrolidin-1-yl)methanone, or a pharmaceutically acceptable salt, solvate or isotopic derivative thereof.

9. The pharmaceutical composition of claim 1, wherein the compound is 2-(6-(2-ethyl-5-fluoro-4-hydroxyphenyl)-1H-indazol-3-yl)-N-methyl-N-phenyl-1,4,6,7-tetrahydro-5H-imidazo[4,5-c]pyridine-5-carboxamide, or a pharmaceutically acceptable salt, solvate or isotopic derivative thereof.

10. A pharmaceutical formulation comprising a pharmaceutically acceptable adjuvant, diluent or carrier and a compound having the structure of Formula Ib,

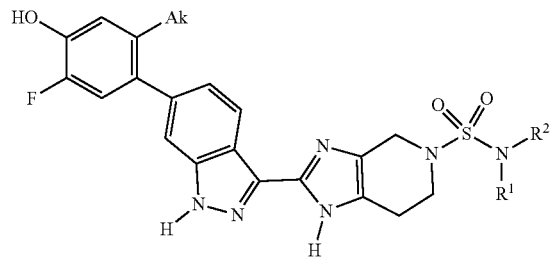

Ib or pharmaceutically acceptable salt, solvate or isotopic derivative thereof, wherein:

X represents halo;

Ak represents $C_{1-6}$ alkyl optionally substituted by one or more fluorine atoms;

$R^1$ and $R^2$ each independently represents H, $C_{1-6}$ alkyl, $C_{3-7}$ cycloalkyl, aryl, heteroaryl, or heterocyclyl, which latter five groups are optionally substituted by one or more substituents selected from halo, cyano, —C(O)OH, oxo, —$NR^3SO_2R^4$, —N=S(O)($R^4$)$_2$, S(O)$_m$$R^5$, —P(O)($R^4$)$_2$, —C(O)$NR^5R^6$, —S(O)$_2$$NR^5R^6$, —(OCH$_2$CH$_2$)$_{10-4}$OR$^5$, —(CH$_2$)$_{0-4}$—$NR^5R^6$, $C_{1-6}$ alkyl, $C_{2-6}$ alkenyl, $C_{2-6}$ alkynyl, $C_{3-7}$ cycloalkyl, aryl, heteroaryl or heterocyclyl, which latter seven groups are optionally substituted by one or more substituents selected from halo, cyano, —C(O)OH, $C_{1-4}$ alkyl, $C_{1-4}$ alkoxy, oxo and hydroxy;

or $R^1$ and $R^2$, together with the N-atom to which they are attached, form a 4- to 7-membered heterocyclic group that is fully saturated or partially unsaturated and which heterocyclic group contains one N atom (the atom to which $R^1$ and $R^2$ are attached) and, optionally, one or more further heteroatoms selected from O, S and N, and which heterocyclic group is optionally fused to a benzene or heteroaromatic ring, and which heterocyclic group is optionally substituted by one or more substituents selected from halo, hydroxy, oxo, —C(O)OH, —$NR^3SO_2R^4$, —S(O)$_m$$R^5$, —C(O)$NR^5R^6$, —(CH$_2$)$_{0-4}$—$NR^5R^6$, —(OCH$_2$CH$_2$)$_{0-4}$OR$^5$, $C_{1-4}$ alkyl, $C_{1-4}$ alkoxy, aryl, heteroaryl, and heterocyclyl, which latter five groups are optionally substituted by one or more substituents selected from halo, cyano, —C(O)OH, $C_{1-4}$ alkyl, $C_{1-4}$ alkoxy, oxo and hydroxy;

$R^3$ represents H or $C_{1-4}$ alkyl optionally substituted by one or more substituents selected from halo, hydroxy and $C_{1-2}$ alkoxy;

$R^4$ represents $C_{1-4}$ alkyl, $C_{3-7}$ cycloalkyl, aryl, heteroaryl or heterocyclyl, which latter five groups are optionally substituted by one or more substituents selected from halo, cyano, —C(O)OH, $C_{1-4}$ alkyl, oxo, hydroxy and $C_{1-4}$ alkoxy;

$R^5$ and $R^6$ each independently represent H, $C_{1-6}$ alkyl, $C_{3-7}$ cycloalkyl, aryl, heteroaryl, or heterocyclyl, which latter five groups are optionally substituted by one or more substituents selected from halo, cyano, —C(O)OH, oxo, hydroxy, $C_{1-4}$ alkyl, $C_{1-4}$ alkoxy, —S(O)$_p$$R^7$, —C(O)$NR^aR^b$ and —(CH$_2$)$_{0-4}$—$NR^aR^b$, or [C($R^{6b}$)($R^{6c}$)CH$_2$Z]$_{1-12}$—CH$_2$CH$_2$—$R^{6a}$ or —C($R^{6b}$)($R^{6c}$)—[$C_{1-5}$ alkylene]-$R^{6a}$;

or $R^5$ and $R^6$, together with the N-atom to which they are attached, form a 4- to 7-membered heterocyclic group that is fully saturated or partially unsaturated and which heterocyclic group contains one N atom (the atom to which $R^5$ and $R^6$ are attached) and, optionally, one or more further heteroatoms selected from O, S and N, and which heterocyclic group is optionally substituted by one or more substituents selected from halo, hydroxy, oxo, —C(O)OH, —S(O)$_p$$R^7$, —C(O)$NR^aR^b$, —(CH$_2$)$_{0-4}$—$NR^aR^b$, —(OCH$_2$CH$_2$)$_{0-4}$OR$^c$, $C_{1-4}$ alkyl, $C_{1-4}$ alkoxy, aryl, heteroaryl and heterocyclyl, which latter five groups are optionally substituted by one or more substituents selected from halo, cyano, —C(O)OH, $C_{1-4}$ alkyl, $C_{1-4}$ alkoxy, oxo and hydroxy;

Z represents, independently upon each occurrence, —O—, —C(O)N($R^8$)— or —N($R^8$)C(O)—;

$R^{6a}$ represents —OR$^{7a}$, —S(O)$_p$$R^7$, —N($R^{7b}$)$R^{7c}$ or —C(O)OH;

$R^{6b}$, $R^{6c}$, and $R^8$ independently represent H or methyl;

$R^a$, $R^b$ and $R^c$ independently represent H or $C_{1-4}$ alkyl optionally substituted by one or more substituents selected from halo, hydroxy and —C(O)OH, or $R^a$ and $R^b$, together with the N-atom to which they are attached, form a 4- to 7-membered heterocyclic group that is fully saturated, partially unsaturated or fully aromatic and which heterocyclic group contains one N atom (the atom to which $R^a$ and $R^b$ are attached) and, optionally, one or more further heteroatoms selected from O, S and N, and which heterocyclic group is optionally substituted by one or more substituents selected from halo, hydroxy, oxo, —C(O)OH, $C_{1-4}$ alkyl, $C_{1-4}$ alkoxy and $C_{1-4}$ hydroxyalkyl;

$R^7$ represents $C_{1-4}$ alkyl optionally substituted by one or more substituents selected from halo, hydroxy and $C_{1-4}$ alkoxy;

$R^{7a}$ to $R^{7c}$ independently represent H or $C_{1-4}$ alkyl optionally substituted by one or more halo atoms or by —C(O)OH, or $R^{7b}$ and/or $R^{7c}$ represents —[$C_a$ alkylene]-[$C_b$ alkylene]-OR$^{7d}$, or $R^{7b}$ and $R^{7c}$ together with the N-atom to which they are attached, form a 4- to 7-membered heterocyclic group that is fully saturated, partially unsaturated or fully aromatic and which heterocyclic group contains one N atom (the atom to which $R^{7b}$ and $R^{7c}$ are attached) and, optionally, one or more further heteroatoms selected from O, S and N, and which heterocyclic group is optionally substituted by one or more substituents selected from halo, hydroxy, oxo, —C(O)OH, $C_{1-4}$ alkyl, $C_{1-4}$ alkoxy and $C_{1-4}$ hydroxyalkyl;

a and b independently represent an integer selected from 1, 2 and 3, wherein the sum of a and b is 2, 3 or 4;

$R^{7d}$ represents H or $C_{1-4}$ alkyl optionally substituted by one or more halo atoms: and m and p represent, independently upon each occurrence, 0, 1 or 2.

11. The pharmaceutical composition of claim 10, wherein X represents fluoro and/or Ak represents $C_{1-3}$ alkyl.

12. The pharmaceutical composition of claim 10, wherein:

$R^1$ and $R^2$ independently represent H, heterocyclyl, $C_{1-2}$ alkyl or phenyl, which latter two groups are optionally substituted by one or more substituents selected from heterocyclyl, halo, cyano, —OR$^5$a and methyl, which latter group is optionally substituted by one or more halo atoms; and $R^{5a}$ represents H or $C_{1-2}$ alkyl.

13. The pharmaceutical composition of claim 10, wherein:

$R^1$ and $R^2$, together with the N-atom to which they are attached, form a 5- or 6-membered heterocyclic group that is fully saturated and which heterocyclic group contains one N atom (the atom to which $R^1$ and $R^2$ are attached) and, optionally, one or two further heteroatoms selected from O, S and N, and which heterocyclic group is optionally fused to a benzene ring, and which heterocyclic group is optionally substituted by one or more substituents selected from halo, oxo, S(O)$_2$$R^{5b}$, $C_{1-3}$ alkyl, $C_{1-3}$ alkoxy and heterocyclyl; and $R^{5b}$ represents $C_{1-2}$ alkyl.

14. The pharmaceutical composition of claim 10, wherein each heterocyclyl group independently represents a 5- or 6-membered heterocyclic ring that is fully saturated, which group contains one or two heteroatoms selected from N, O and S.

15. The pharmaceutical composition of claim 1, wherein the compound is:

5-ethyl-2-fluoro-4-(3-(5-((4-(methylsulfonyl)piperazin-1-yl)sulfonyl)-4,5,6,7-tetrahydro-1H-imidazo[4,5-c]pyridin-2-yl)-1H-indazol-6-yl)phenol;

1-((2-(6-(2-ethyl-5-fluoro-4-hydroxyphenyl)-1H-indazol-3-yl)-6,7-dihydro-1H-imidazo[4,5-c]pyridin-5 (4H)-yl)sulfonyl)-N-methylpiperidine-4-carboxamide;

5-ethyl-2-fluoro-4-(3-(5-((4-m ethylpiperazin-1-yl)sulfonyl)-4,5,6,7-tetrahydro-1H-imidazo[4,5-c]pyridin-2-yl)-1H-indazol-6-yl)phenol; or 4-((2-(6-(2-ethyl-5-fluoro-4-hydroxyphenyl)-1H-indazol-3-yl)-6,7-dihydro-1H-imidazo[4,5-c]pyridin-5 (4H)-yl)sulfonyl)piperazine-1-carbaldehyde;

or a pharmaceutically acceptable salt, solvate or isotopic derivative thereof.

16. The pharmaceutical composition of claim 10, wherein the compound is N-(2-cyanoethyl)-2-(6-(2-ethyl-5-fluoro-4-hydroxyphenyl)-1H-indazol-3-yl)-N-(2-methoxyethyl)-6,7-dihydro-1H-imidazo[4,5-c]pyridine-5(4H)-sulfonamide, or a pharmaceutically acceptable salt, solvate or isotopic derivative thereof.

17. The pharmaceutical composition of claim 1, wherein the compound is 2-(6-(2-ethyl-5-fluoro-4-hydroxyphenyl)-1H-indazol-3-yl)-N-methyl-N-(tetrahydro-2H-pyran-4-yl)-6,7-dihydro-1H-imidazo[4,5-c]pyridine-5(4H)-sulfonamide, or a pharmaceutically acceptable salt, solvate or isotopic derivative thereof.

18. The pharmaceutical composition of claim 1, wherein the compound is 5-ethyl-2-fluoro-4-(3-(5-(pyrrolidin-1-ylsulfonyl)-4,5,6,7-tetrahydro-1H-imidazo[4,5-c]pyridin-2-yl)-1H-indazol-6-yl)phenol, or a pharmaceutically acceptable salt, solvate or isotopic derivative thereof.

19. The pharmaceutical composition of claim 1, wherein the compound is 5-ethyl-2-fluoro-4-(3-(5-(morpholinosulfonyl)-4,5,6,7-tetrahydro-1H-imidazo[4,5-c]pyridin-2-yl)-1H-indazol-6-yl)phenol, or a pharmaceutically acceptable salt, solvate or isotopic derivative thereof.

20. The pharmaceutical composition of claim 1, wherein the compound is 4-((2-(6-(2-ethyl-5-fluoro-4-hydroxyphenyl)-1H-indazol-3-yl)-6,7-dihydro-1H-imidazo[4,5-c]pyridin-5(4H)-yl)sulfonyl)thiomorpholine 1,1-dioxide, or a pharmaceutically acceptable salt, solvate or isotopic derivative thereof.

21. The pharmaceutical composition of claim 1, wherein the compound is 5-ethyl-2-fluoro-4-(3-(5-((4-methoxypiperidin-1-yl)sulfonyl)-4,5,6,7-tetrahydro-1H-imidazo[4,5-c]pyridin-2-yl)-1H-indazol-6-yl)phenol, or a pharmaceutically acceptable salt, solvate or isotopic derivative thereof.

* * * * *